United States Patent
Ahmad et al.

(10) Patent No.: US 10,476,821 B2
(45) Date of Patent: Nov. 12, 2019

(54) SYSTEM AND METHOD FOR SECURE MESSAGING

(71) Applicant: ANTHELIO HEALTHCARE SOLUTIONS INC., Dallas, TX (US)

(72) Inventors: Asif Ahmad, The Woodlands, TX (US); David Raju Manne, Dallas, TX (US); Pranam Ben, Maitland, FL (US)

(73) Assignee: ATOS DIGITAL HEALTH SOLUTIONS, INC., Dallas, TX (US)

( * ) Notice: Subject to any disclaimer, the term of this patent is extended or adjusted under 35 U.S.C. 154(b) by 1057 days.

(21) Appl. No.: 14/723,157

(22) Filed: May 27, 2015

(65) Prior Publication Data

US 2015/0286790 A1    Oct. 8, 2015

Related U.S. Application Data

(63) Continuation-in-part of application No. 14/322,713, filed on Jul. 2, 2014.
(Continued)

(51) Int. Cl.
*H04L 12/58* (2006.01)
*G06F 17/27* (2006.01)
(Continued)

(52) U.S. Cl.
CPC ........ *H04L 51/046* (2013.01); *G06F 17/2705* (2013.01); *G06F 17/277* (2013.01);
(Continued)

(58) Field of Classification Search
None
See application file for complete search history.

(56) References Cited

U.S. PATENT DOCUMENTS

| 2004/0193448 A1 | 9/2004 | Woodbridge et al. |
| 2009/0080408 A1* | 3/2009 | Natoli ............ H04L 45/00 370/351 |

(Continued)

OTHER PUBLICATIONS

Non-Final Office Action dated Nov. 30, 2017 for U.S. Appl. No. 14/322,713.

(Continued)

*Primary Examiner* — Jonathan Ng
*Assistant Examiner* — Rachelle L Reichert
(74) *Attorney, Agent, or Firm* — Miles & Stockbridge, P.C.

(57) ABSTRACT

Disclosed herein is a secure messaging engagement hub for structuring of unstructured electronic messages. The secure messaging engagement hub has a natural language processor that structures an unstructured electronic message. The natural language processor structures the unstructured electronic message by using a lexical parser to parse free text within the unstructured electronic message. The natural language processor also may tokenize the parsed free text into tokens representing components of the parsed free text. Message component n-grams are generated based on the tokens representing the components of the parsed free text. The tokens are coded with various metadata tags based on an analysis of the tokens. The metadata tags indicate message components of the tokens. And a structured electronic message corresponding to the unstructured electronic message is generated, the structured electronic message comprising the tokens and the metadata tags.

18 Claims, 13 Drawing Sheets

Related U.S. Application Data

(60) Provisional application No. 61/841,994, filed on Jul. 2, 2013.

(51) Int. Cl.

| | | |
|---|---|---|
| *G16H 10/60* | (2018.01) |
| *G16H 40/20* | (2018.01) |
| *G06Q 10/10* | (2012.01) |
| *G06Q 50/22* | (2018.01) |
| *G06F 19/00* | (2018.01) |

(52) U.S. Cl.
CPC ............. *G06F 19/00* (2013.01); *G16H 10/60* (2018.01); *G16H 40/20* (2018.01); *G06Q 10/107* (2013.01); *G06Q 50/22* (2013.01)

(56) References Cited

U.S. PATENT DOCUMENTS

| | | | | |
|---|---|---|---|---|
| 2009/0256701 A1 | | 10/2009 | Chamberlain et al. | |
| 2010/0137693 A1* | | 6/2010 | Porras ..................... | A61M 1/16 600/301 |
| 2010/0185651 A1* | | 7/2010 | Crow ................ | G06F 17/30716 707/769 |
| 2012/0101847 A1 | | 4/2012 | Johnson et al. | |
| 2012/0166212 A1* | | 6/2012 | Campbell ............. | G06F 19/328 705/2 |
| 2013/0179193 A1 | | 7/2013 | Perez et al. | |
| 2013/0197940 A1* | | 8/2013 | Garber .................. | G06F 19/322 705/3 |
| 2013/0290027 A1* | | 10/2013 | Tang ...................... | G06F 19/322 705/3 |
| 2015/0347422 A1* | | 12/2015 | Fadel ................ | G06F 17/30389 707/767 |
| 2016/0037345 A1 | | 2/2016 | Margadoudakis | |

OTHER PUBLICATIONS

Advisory Action dated Aug. 18, 2017 for U.S. Appl. No. 14/322,713.
Final Office Action dated Jun. 7, 2017 for U.S. Appl. No. 14/322,713.
Non-Final Office Action dated Oct. 20, 2016 for U.S. Appl. No. 14/322,713.
Final Office Action dated Jul. 6, 2018 for U.S. Appl. No. 14/322,713.
Non-Final Office Action dated Apr. 2, 2019 for U.S. Appl. No. 14/322,713.
Final Office Action dated Aug. 7, 2019 issued in U.S. Appl. No. 14/322,713.

\* cited by examiner

SYSTEM AND METHOD FOR SECURE MESSAGING

CROSS-REFERENCE TO RELATED APPLICATIONS

This application is a continuation-in-part of U.S. patent application Ser. No. 14/322,713, filed on Jul. 2, 2014, entitled "System and method for patient engagement," which claims priority to U.S. Provisional Application No. 61/841,994, filed on Jul. 2, 2013, entitled "Patient Information System and Method," both of which are hereby incorporated herein by reference in their entirety.

FIELD OF THE DISCLOSURE

In general, the present disclosure relates to secure electronic messaging. More specifically, the present disclosure relates to enabling secure electronic message functionality compliant with medical digital privacy standards.

BACKGROUND

Patient privacy is an important aspect of healthcare. Government regulations place strict guidelines on the sharing of medical data. The Health Insurance Portability and Accountability Act (HIPAA) of 1996 introduced strict rules regarding the sharing of individually identifiable health information. The introduction of the internet and electronic communication has led to new problems in the sharing of personal health information. Some of this information cannot be given over the telephone or transmitted in an email because of its sensitive nature. Further, there are times when a patient needs to relay electronic medical information to another provider or an in-home caretaker or some other third party. Thus, electronic communications between a patient and provider can be difficult to accomplish, and current online communication networks, hubs, and components for messaging are not sufficient technological solutions.

SUMMARY

The system and method described herein introduces approaches for providing dynamic and secure communication overcoming the problems presented with current online communication networks, hubs, and components for messaging. Electronic messages may be transmitted and received in various formats. Some formats may include free text fields and other data that may be considered unstructured. Unstructured electronic messages may be difficult to search and categorize by electronic messaging systems. In some cases, it may be useful to add structure to unstructured electronic messages. These approaches may include parsing and tokenizing free text within an unstructured electronic message, and then coding the parsed, tokenized n-grams as a basis for forming structured messages for dynamic and secure communications. These approaches may also include allowing both Direct protocol and in-network communications through the same network hub. Providing both formats in the same hub may allow users to seamlessly communicate using either Direct protocol or secure in-network messaging without changing to a different messaging platform. Providing both formats may also allow for ease of adding additional third-parties to messaging sessions regardless of the messaging format used by the third party.

This secure communication may be compliant with regulations governing the communication of personal medical information. The system and method may also provide a means for secure messaging from the provider to a third party authorized by the patient. In addition, the messages may be anonymized and organized by subject. The medical provider may then use the organized messages to recognize trends in treatment or other commonalities in a group of patients. Finally, the messages may be automatically appended to a patient's electronic medical record for archival and historical purposes.

Communication may play a key role in the treatment process between a care delivery team facilitating a speedy recovery for a patient. Patients may appreciate an extra communication with a care provider to discuss health issues. Care providers may also want to spend additional time with patients but may be unable to due to demands upon their schedule. Engaging a patient in their care process may be a key component for hospitals and care providers to achieve a healthy living for patients. The channel of communication between patients and health care providers must be well secured in order to keep health information of patients confidential.

BRIEF DESCRIPTION OF THE DRAWINGS

Reference is now made to the following detailed description of the preferred embodiments, taken in conjunction with the accompanying drawings. It is emphasized that various features may not be drawn to scale. In fact, the dimensions of various features may be arbitrarily increased or reduced for clarity of discussion. In addition, it is emphasized that some components be omitted in certain figures for clarity of discussion. Reference is now made to the following descriptions taken in conjunction with the accompanying drawings, in which.

These exemplary figures and embodiments are to provide a written, detailed description of the embodiments set forth by any claims that issue from the present application. These exemplary figures and embodiments should not be used to limit any claims that ultimately issue in a patent from the present application.

DETAILED DESCRIPTION

Approaches for providing dynamic and secure communication overcoming the problems presented with current online communication networks, hubs, and components for messaging are provided below. These approaches include parsing and tokenizing free text within an unstructured electronic message, and then coding the parsed, tokenized n-grams as a basis for forming structured messages for dynamic and secure communications. These approaches also include allowing both direct and in-network communications through the same network hub, to allow for users to seamlessly communicate using either Direct protocol or secure in-network messaging without changing to a different messaging platform.

Although the disclosed embodiments are presented in the context of patient and provider communication, the approaches disclosed herein could be used in a variety of contexts in which dynamic and secure communication overcoming the problems presented with current online communication networks, hubs, and components for messaging are desired.

A secure system for patient engagement may be desirable for interacting with patients in a healthcare environment to overcoming technological shortcomings of current online or networked systems and provide for enhanced secure and dynamic messaging. In some embodiments, the secure system may be configured to comply with government regulations, for example the Health Insurance Portability and Accountability Act of 1996 (HIPAA). Training, games, and other media may be tailored to a specific condition that a patient is suffering from or interested in. When a patient visits a health care provider, various forms may be auto populated based on information the patient has stored at a patient engagement hub. These communications may occur over a provider's network to a mobile device, or via secured channels over the internet, or over any other suitable communication medium. As used herein, mobile device may refer to transportable devices such as mobile telephones, smartphones, personal digital assistants, handheld devices, tablets, nettops, or laptop computers, and similar devices that have mobile communications capabilities. Networks may include routers, hubs, switches, firewalls, content switches, gateways, call controllers, and/or any other suitable components in any suitable form or arrangement. Networks may include, in whole or in part, one or more secured and/or encrypted Virtual Private Networks (VPNs) operable to couple one or more network elements together by operating or communicating over elements of a public or external communication network.

Figure 1:
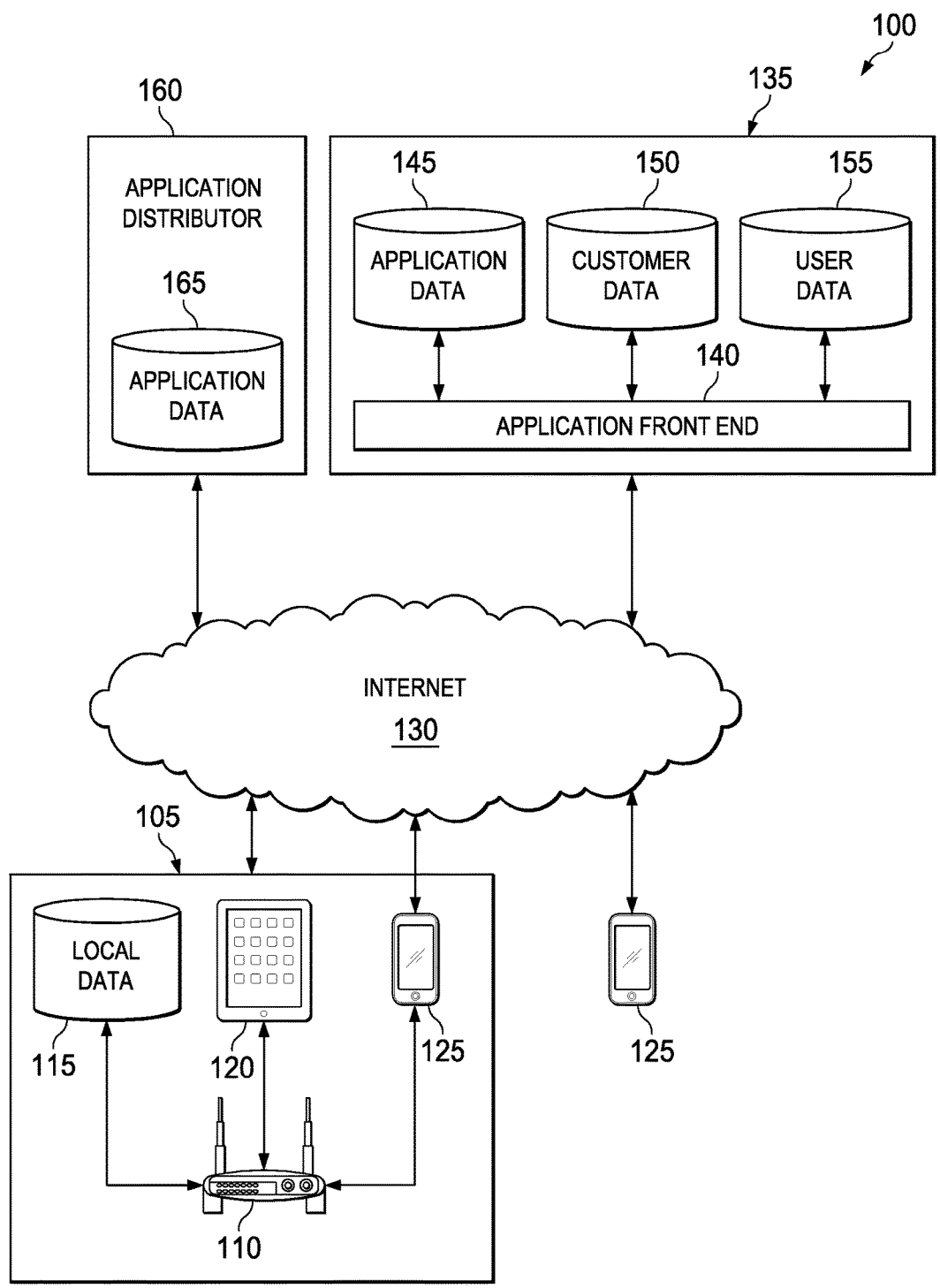
FIG. 1 is a diagram of an embodiment of a system for patient engagement.

Turning now to FIG. 1, a diagram of an embodiment of a system for patient engagement 100 is shown. A user may visit a customer location 105. Customer location 105 may be a health plan, a medical provider, a hospital, or any other location related to receiving healthcare treatment. Customer location 105 may provide WiFi access via router 110. Router 110 may provide a WiFi network connection, or any other technology that may be used to connect to a network, e.g., Bluetooth or wired Ethernet. Router 110 may allow users to access local data 115. Local data 115 may include consent forms or enrollment forms that need to be completed by the user or any other forms provided by the customer to the user.

In order to access local data 115 or other patient engagement material, a customer may provide a customer mobile device 120 to users that visit customer location 105. Customer mobile device 120 may be configured to access local data 115 via router 110. Usage of the customer mobile device 120 may be anonymous. If a user chooses to enter personally identifiable information (PII) or protected health information (PHI) into the local mobile device 110, the session may no longer be anonymous and the customer may be able to provide additional information tailored to the user of the customer mobile device 120. In any case customer mobile device 120 may be owned or provided by the customer for the use of the user and no personally identifiable information or protected health information may be stored on the customer mobile device 120.

Customer mobile device 120 may access information stored at patient engagement hub 135. Patient engagement hub 135 may contain an application front end 140 for interfacing with an instance of a point of service (POS) patient engagement application running on customer mobile device 120. Application front end 140 may also interact with application data 145, customer data 150, and user data 155. Access to the patient engagement hub 135 may be controlled by a unique identifier assigned to customer mobile device 120, e.g. a whitelist containing the MAC address of the customer mobile device 120. Application data 145 may include training materials, games, and other data that may be used by instances of patient engagement applications across many customer locations. Customer data 150 may contain data related to the customer, e.g., name, location, MAC addresses of customer mobile devices, etc. User data 155 may contain personally identifiable information and protected health information of end users. Each of application data 145, customer data 150, and user data 155 may be encrypted and transmitted in accordance with government standards to protect the privacy of users' data.

In some cases a user may install a mobile patient engagement application on their own user mobile device 125. The mobile patient engagement application may allow a user to access features of the patient engagement hub 135 via the internet using a user mobile device 125 that is not in a customer location 105. For example, a user may update user data 155 or access application data 145 from a remote location via user mobile device 125. User may download the mobile patient engagement application from an application distributor 160. Application distributor 160 may store the code required to install and execute the mobile patient engagement application or the POS patient engagement application in application data store 165. The components of the system for patient engagement 100 will be discussed in greater detail in the following sections.

Figure 2:
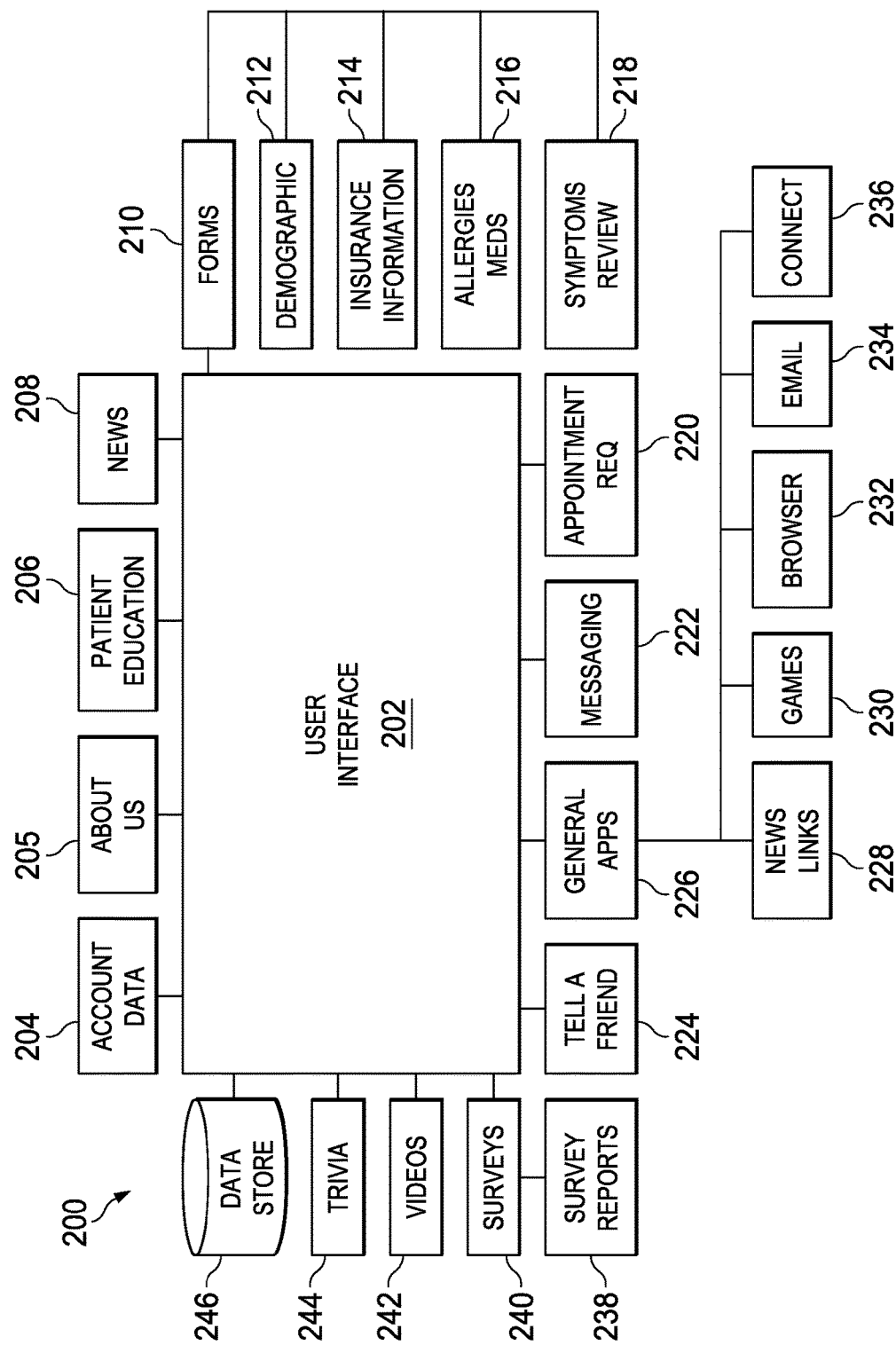
FIG. 2 is a functional block diagram of an embodiment of a patient engagement hub.

FIG. 2 is a diagram of an embodiment of a patient engagement hub 200 is provided. A user interface 202 may allow a user or client to access the various modules of patient engagement hub 200. The data related to each of the modules and other components of the patient engagement hub 200 may be stored in a data store 246. While a single data store 246 is shown, in some embodiments, multiple data store 246 may be used as required.

Account data module 204 may be configured to store customer data. The account data module 204 may be accessed by clicking a my account link, or some other link, after logging into the patient engagement hub 200. In this module a customer may update their email address, change their password, and name an administrator for the customer's patient engagement hub 200 account. The customer may also edit their facility (e.g. customer location 105) information. Facility information may include a facility name, address, contact numbers, contact emails, hours of operation and/or a facility logo. Customers may also update their social preferences. For example, customers may give users additional data using social networking profiles for patients to view. In order to direct users to the correct sites, the customer may need to enter their website, Facebook, Twitter, and/or other social media accounts into account data module 204. The location entered by the customer may be where the user will be directed if they touch the Facebook, Twitter, or other social media icons in the footer of the POS patient engagement application or the mobile patient engagement application. The account data module 204 may also allow a customer to customize a ticker message that may appear in the POS patient engagement application or the mobile patient engagement application. A further function of account data module 204 may include information regarding usage of the modules by users. The information may include total number of views, identification of patients that have viewed, and data/time of viewing. Various reports may be generated based on the usage information. There may also be tracking of RSVPs to events and invites advertised on the POS patient engagement application or the mobile patient engagement application.

The about us module 205 may allow a customer to add content that includes visual enhancements like graphics and videos to deliver an interactive personalized user experience to their targeted audience when users access the POS patient engagement application or the mobile patient engagement application at the customer location. The about us module 205 may include a logo and description of the customer. Additionally, the about us module may include free text boxes that allow the customer to "Add", "Edit", or "Delete". The customer may add textual descriptions of important information relevant to users of the POS patient engagement application or the mobile patient engagement application at the customer location. If the customer selects the "Add" button at the bottom of the queue, a free text box may be added to the queue. If customer selects the "Edit" button, the free text box may become editable to enter or clear any information in the existing free text box. If the customer clicks on the "Delete" button, a pop-up may appear requesting the customer to confirm that they would like to delete the item. The about us module 205 may also include videos selected by the customer to be displayed to users of the POS patient engagement application or the mobile patient engagement application. The videos may be stored in customer data 150, or links may be provided to other locations storing the videos. In addition to videos, customers may upload photos to the about us module 205. Similar to videos, photos may be stored in customer data 150, or links may be provided to other locations storing the photos. Lastly, the about us module 205 may be used to store links to websites relevant to users at the customer location, e.g., links to online bill payments or links to a customer website.

Patient education module 206 is an information module that may comprise two components, health videos and user defined. This module may serve as a delivery mechanism for engaging patients to improve health education using interactive videos and other customizable educational material. The customer may add any videos to convey educational content to users. The videos may relate directly to specific conditions treated by the customer. These videos may then be presented to users with the conditions. Videos may be uploaded or a link to videos at other locations may be provided. As part of this module, statistics may be kept for the customer to view. The statistics may include the number of times a video has been shared. The customer defined module of the patient education module 206 allows the customer to present any other training materials that may be relevant to conditions users may be concerned with, e.g., reading materials and links to websites with useful information.

The news and events module 208 is an information module that may serve as a way for customers to share news and events related to the customer with users. A queue of articles that may be displayed to users is provided for editing by the customer. Another queue containing upcoming events that may be relevant to the users is also displayed to the customer for editing. Events may be automatically removed from the queue 48 hours after their scheduled completion. The events may offer an RSVP function for users to inform the customer or event organizer of their intent to attend the event.

The patient forms module 210 allows a customer to upload and store various forms that users may need to complete. The customer may upload various consent forms or other forms that may be required for treatment. Statistics may be collected for forms most viewed, number of views, and number of patient updates to forms. Patient updates may include times when the user updates the form data and submits it locally to the customer prior to treatment. The forms module 210 may contain several sub-modules. The demographics module 212 may allow the customer to select certain fields related to demographic that should be default in certain forms. For example, some forms may require date of birth. This demographic form field may be selected by the customer as a required field for those forms. The insurance information module 214 may allow the customer to require certain fields related to insurance in certain forms. For example, insurance company name may be a required field on the customer's forms. The allergies and medications module 216 may allow a customer to require certain fields related to allergies and medications used by a user in their forms. For example, the customer may require an allergy field on all forms that requires users to enter any allergies they may suffer from. The symptom review module 218 may allow a customer to require certain form fields related to symptoms a user may be experiencing. Rather than present all available symptoms to a user, the customer may tailor symptoms fields of a form to areas that the customer treats. For example, a foot doctor may not include form fields for cardiovascular issues.

The appointment request module 220 allows a customer to present an appointment request form to users and to view all pending appointment requests by users. The appoint request module may also provide an archive for past appointment requests that have already been scheduled or deleted by the customer. The fields shown to the customer may include patient name, symptoms, requested dates/times of appointments and other relevant information for scheduling an appointment. The appointment requests may be made using either the POS patient engagement application or the mobile patient engagement application. Statistics may be provided to the customer to include number of pending requests and number of requests received.

The messaging module 222 allows for secure communication between the customer and a user. This communication may be configured to be compliant with government regulations regarding patient privacy, e.g. HIPAA. All messaging occurs within the patient engagement system in order to remain secure, e.g. between one of the patient engagement applications and the patient engagement hub 200. The messaging module may also receive messages via other modules within the patient engagement hub 200. For example, a message may be generated from the news and events module 208 when a user RSVPs to an event. Messages may also include other useful demographic information such as phone number or name of the user.

The tell a friend module 224 is an information module that may allow a customer to configure options for a user to share information with a friend or other acquaintance via the patient engagement system 100. There may be default language that is automatically populated in a message generated by this module. The customer may configure this default language as needed. An additional function of the tell a friend module 224 may allow the customer to select the methods a user may use to tell a friend. For example, a user may tell a friend via email or via a social network.

The survey module 240 is an information module that may allow a customer to create a survey to share with users via the POS patient engagement application or the mobile patient engagement application. The survey may be directed to any number of areas as selected by the customer. The survey report module 238 may retrieve user responses from surveys and provide a report to the customer.

The videos module 242 is an information module that may provide an area for the customer to share other videos not related to patient education with users. For example, general health and fitness videos, children's entertainment, or other videos that a user may be interested in while visiting the customer location.

Trivia module 244 is an information module that may provide an area for customer to create trivia questions and games for users. The trivia may be related to various medical conditions and may be tailored to the user's specific conditions or interests. Statistics may be collected on usage of the trivia and success of users of the trivia.

The general applications module 226 is an information module that may provide an area for the customer to provide the user with other useful applications that a user may be interested in while waiting to see the customer. Other information modules include the news links module 228, which may provide access to national news websites and may also provide news tailored to the users medical conditions, the games module 230, which may provide games to entertain the user, the browser module 232, which may enable a user to browse the world wide web, including potentially with suggested sites. An email module 234 may also be provided to allow the user to access certain email providers, e.g. Hotmail, Gmail, Yahoo, etc. Another information module is the connect module 236, which provides access to social media sites for the user, potentially including suggested social media interactions.

The patient engagement hub 200 acts as a backend for customers to configure what a user may encounter upon accessing the POS patient engagement application or the mobile patient engagement application. Not all modules may be available at every customer location and not all modules may be available at every POS patient engagement application or every mobile patient engagement application. The content of the modules may vary between customer locations based upon the configuration applied by the customers. Further content received at each POS patient engagement application or mobile patient engagement application may vary based upon the user configurations and inputs. The modules presented may be based upon the needs of the customer or user.

Figure 3:
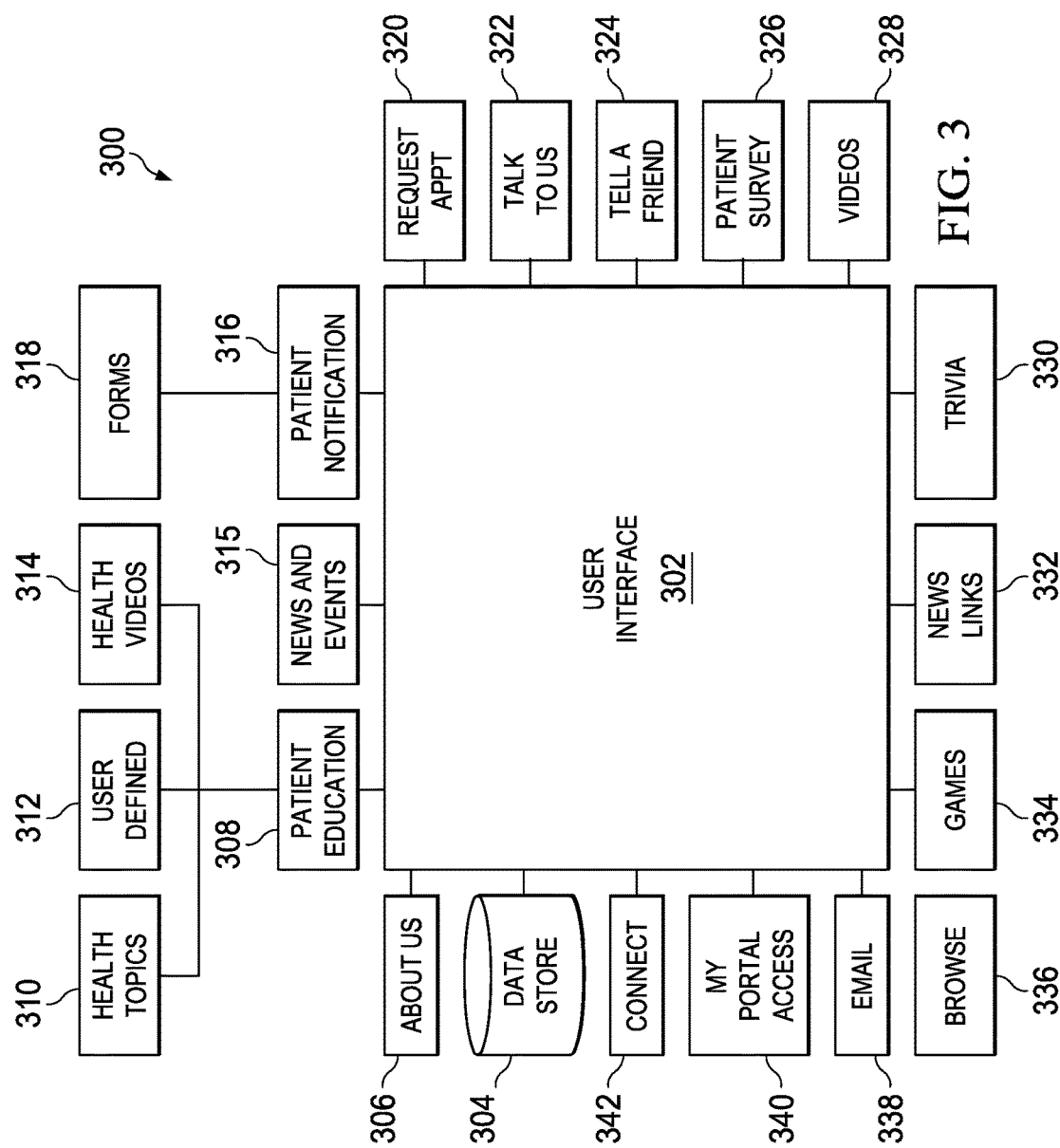
FIG. 3 is a functional block diagram of an embodiment of a patient engagement point of service application.

FIG. 3 is a diagram of an embodiment of a POS patient engagement application 300. POS patient engagement application 300 may be provided to a user at a customer location, e.g., via a customer mobile device 120. The various modules of the POS patient engagement application 300 may be accessed by users via user interface 302. User interface 302 may retrieve components of the various modules from data store 304. User interface 302 may retrieve other components of the various modules from patient engagement hub 200. Thus, in some embodiments, the configurations a customer makes at the patient engagement hub 200 may control the experience a user may experience while using POS patient engagement application 300.

The about us module 306 may provide a user with information about the customer they are visiting. The information presented to the user may be configured by the customer using the about us module 205 of the patient engagement hub 200. In some embodiments, the user may be presented with several tabs or views, e.g., logo, practice description, what you need to know, and/or videos.

The patient education module 308 may provide a user with resources for health related education. The information presented to the user may be configured by the customer using the patient education module 206 of the patient engagement hub 200. In some embodiments, the user may be presented with several sub-modules, health topics module 310, user defined module 312, and health videos module 314.

The health topics module 310 may link to an interactive section providing selectable training. The user may select various body parts and receive training tailored to that body part. The user may select a living better tab that may provide wellness information for the user. Lastly, the user may select a chronic conditions tab that may provide training related to chronic conditions that the user selects.

The user defined module 312 may be completely customized by the customer or by an automated process to provide training directly related to the user. For example, if the user suffers from foot problems, the user defined module 312 may provide training directed to foot problems. The customer may configure this content, or the patient engagement hub 200 may comprise logic for determining what training to provide to a user based upon that user's protected health information.

The health videos module 314 may provide videos related to health to the user. Users may select videos based on favorites, most viewed, or most recently watched. The user may provide ratings on videos based on usefulness and/or entertainment value. The customer may receive the ratings and modify the selection of videos presented to users appropriately.

The news and events module 315 may provide a virtual bulletin board for the customer to share current news and upcoming events with the user. The information presented to the user may be configured by the customer using the news and events module 208 of the patient engagement hub 200. In some embodiments, the user may be presented with relevant notices by the customer, e.g. office closures, new hires, etc. The user may also be presented with a list of upcoming events. If required, the user may RSVP to an upcoming event from the news and events module 315. The upcoming events may be presented in a calendar format or list format or other formats chosen by the user or the customer. The user may message the customer directly from this module with questions related to upcoming events.

The patient notification module 316 may provide a user with notifications and/or forms that the customer has provided for them, e.g. consent forms. The information presented to the user may be configured by the customer using the forms module 210 of the patient engagement hub 200. In some embodiments, the user may choose to anonymously view the forms and subsequently digitally sign them for use by the customer. In some embodiments, the forms may be prepopulated with user personally identifiable information or protected health information when the user accesses the my portal access module 340. The my portal access module is described in further detail in a subsequent section. Additionally, a user may request to have forms or notices emailed to them by entering an email address or retrieving a stored email address via the my portal access module 340.

The appointment request module 320 may provide a user with means for requesting an appointment with the customer. The information presented to the user may be configured by the customer using the appointment request module 220 of the patient engagement hub 200. In some embodiments, the user may be presented with options for selecting one or more desired appointment times. In addition, the user may enter an explanation of the reasons for the appointment request.

The talk to us module 322 may provide a user with a virtual comment box. The information presented to the user may be configured by the customer using the messaging module 222 of the patient engagement hub 200. In some embodiments, the user may provide comments and/or recommendations to the customer either anonymously or the user may enter personally identifiable information if they would like a response from the customer.

The tell a friend module 324 may provide a user with the ability to share their experience at the customer location with friends and/or acquaintances via email and/or social media. The information presented to the user may be configured by the customer using the tell a friend module 224 of the patient engagement hub 200.

The patient survey module 326 may provide a user with surveys created by or provided by the customer. The information presented to the user may be configured by the customer using the surveys module 240 of the patient engagement hub 200. In some embodiments, the user may receive simple yes or no answer questions, or open-ended questions. The user may be able to provide additional feedback via the messaging module 222 directly from the patient survey module 326.

The video module 328 may provide videos for user viewing. The information presented to the user may be configured by the customer using the videos module 242 of the patient engagement hub 200. In some embodiments, the user may be presented with videos that the customer has selected. The videos may be selected by the customer for various reasons, e.g., entertainment, general health facts, and/or advertisements for products or studies. Users may choose videos based on favorites, most viewed, or most recently viewed. The user may also rate the videos and provide feedback to the customer regarding the videos.

The trivia module 330 may provide a user with a trivia game. The information presented to the user may be configured by the customer using the trivia module 244 of the patient engagement hub 200. In some embodiments, the user may be presented with trivia questions selected by the customer to relate to conditions treated by the customer. In some embodiments, trivia questions may be selected automatically based upon protected health information of the user stored at the patient engagement hub 200, in these embodiments, a user may be required to log in using the my portal access module 340.

The news links module 332 may provide a user with links to various news websites or electronic reader based magazines. The information presented to the user may be configured by the customer using the news links module 228 of the patient engagement hub 200. In some embodiments, a customer may cut back on the need to keep magazines in the customer location by providing the news links. The news links may also provide for up to date news, rather than an outdated magazine that may be present in a customer location.

The games module 334 may provide a user with information about the customer they are visiting. The information presented to the user may be configured by the customer using the games module 230 of the patient engagement hub 200. In some embodiments, the user may be presented with various games for use when the user may desire a break from learning.

The browse module 336 may provide a user with a web browser or links to certain websites. The information presented to the user may be configured by the customer using the browser module 232 of the patient engagement hub 200. In some embodiments, the user may be presented with the customer's website or other websites the customer finds appropriate to share with users. In other embodiments, the user may be presented with access to a web browser for browsing the world wide web.

The email module 338 may provide a user with access to web-based email providers. The information presented to the user may be configured by the customer using the email module 234 of the patient engagement hub 200. In some embodiments, the user may be presented with several links to web-based email providers, e.g. yahoo, Gmail, Hotmail, and/or other providers. The user may select a provider and log in to view their personal email account.

The connect module 342 may provide a user with access to social media sites. The information presented to the user may be configured by the customer using the connect module 236 of the patient engagement hub 200. In some embodiments, the user may be presented with links to several social media sites, e.g., linkedin, foursquare, facebook, twitter, and/or other social media websites. By choosing a link, a user may be provided access to the social media site where the user may log onto their personal social media account.

The my portal access module 340 may provide a user with a log-in option providing consent for the customer to access the user's protected health information to customize the user experience with the POS patient engagement application 300. The user may be directed to a single sign on page for the customer's selected portal for accessing protected health information. Users may be required to enter a user name and a HIPAA compliant password to access the user protected health information data. Accessing the my portal access module 340 may allow the user to have certain forms prepopulated based on previously stored protected health information. The user may also update personally identifiable information or protected health information via this or other modules after successful authentication.

Figure 4:
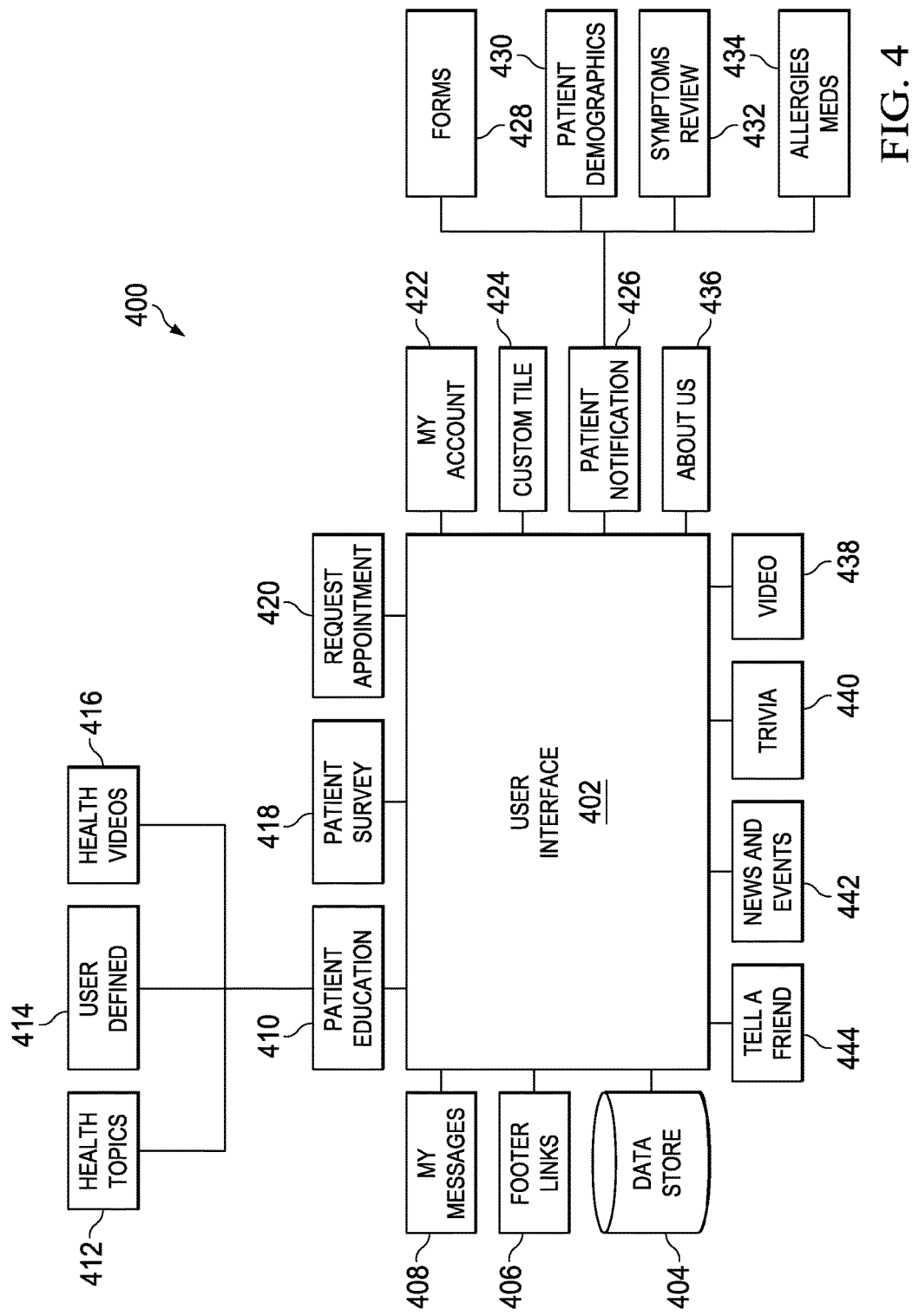
FIG. 4 is a functional block diagram of an embodiment of a patient engagement mobile application.

FIG. 4 is a diagram of an embodiment of a mobile patient engagement application 400. Mobile patient engagement application 400 may be downloaded by a user to their personal device, e.g., a customer mobile device 125. After a user downloads and installs the mobile patient engagement application 400 they may either create a new user account or access an existing user account. Creating a new account may require selecting a username and password and/or entering some personally identifiable information.

The various modules of the mobile patient engagement application 400 may be accessed by users via user interface 402 after logging into the mobile patient engagement application 400. User interface 402 may retrieve components of the various modules from data store 404. User interface 402 may retrieve other components of the various modules from patient engagement hub 200. Thus, in some embodiments, the configurations a customer makes at the patient engagement hub 200 may control the experience a user may have while using mobile patient engagement application 400. In some embodiments, the POS patient engagement application may be configured to be anonymous in nature, while the mobile patient engagement application may be configured to be logged into by a user and thus may not be anonymous. In these embodiments, content provided to the user via the mobile patient engagement application may be tailored specifically to the user by the customer or by other automated processes that select content based upon characteristics of the user, e.g. personally identifiable information or protected health information.

Several of the modules in the mobile patient engagement application 400 may perform in a substantially similar manner to modules provided in the POS patient engagement application 300. Patient education module 410 may correspond to patient education module 308; health topics module 412 may correspond to health topics module 310; user defined module 414 may correspond to user defined module 312; health videos module 416 may correspond to health videos module 314; patient survey module 418 may correspond to patient survey module 326; appointment request module 420 may correspond to appointment request module 320; about us module 436 may correspond to about us module 306; video module 438 may correspond to video module 328; trivia module 440 may correspond to trivia module 330; news and events module 442 may correspond to news and events module 315; and tell a friend module 444 may correspond to tell a friend module 324.

The footer links module 406 may provide a user with shortcuts to frequently-used web links. The information presented to the user may be configured by the customer using the patient engagement hub 200. In some embodiments, the user may be presented with links to web media sites, e.g., social media, a home page link, a code of conduct icon, or other links as determined by a customer and/or user. By choosing a link, a user may be provided access to the social web site.

The my messages module 408 may provide a user with access to communications tools that may allow the user to contact the customer via secure messaging in real time or via an email-like system. The information presented to the user may be configured by the customer using the messaging module 222 of the patient engagement hub 200. The my messages module 408 may provide secure government regulation (e.g. HIPAA) compliant messaging between a user and customer.

The my account module 422 may allow a user to access and update account information. The user may update a username or password, security questions, or request disenrollment from the mobile patient engagement application. This module may also be used to update certain patient demographics.

The custom tile module 424 may provide a fully customizable module for use by the customer. The custom tile module may be used by the customer to provide the user with a log on to an existing platform/portal for accessing protected health information.

The patient notification module 426 may provide a user with access to customer provided notifications, forms, and/or other data. The patient notification module may contain several sub-modules: forms module 428; patient demographics module 430; symptoms review module 432, and allergies and medications module 434. The information provided by the user to the sub-modules may be used by customers to provide tailored healthcare information to the user related specifically to symptoms the user is experiencing; conditions users with similar demographics experience; and/or information related to allergies and medications the user may be taking. This information may also allow a customer to prepare before-hand for a user visit.

The forms module 428 may provide a user with access to forms or notifications provided by the customer. The information presented to the user may be configured by the customer using the forms module 210 of the patient engagement hub 200. The forms may include consent forms for treatment, privacy notices, or other forms for use by the customer.

The patient demographics module 430 may allow a user input and/or update demographic information. The information presented to the user may be configured by the customer using the demographics module 212 of the patient engagement hub 200.

The symptoms review module 432 may allow a user to indicate symptoms that they may be experiencing. The information presented to the user may be configured by the customer using the symptoms review module 218 of the patient engagement hub 200.

The allergies and medications module 434 may allow a user to indicate allergies they may have or medications they may be currently taking. The information presented to the user may be configured by the customer using the allergies and medications module 216 of the patient engagement hub 200.

Figure 5:
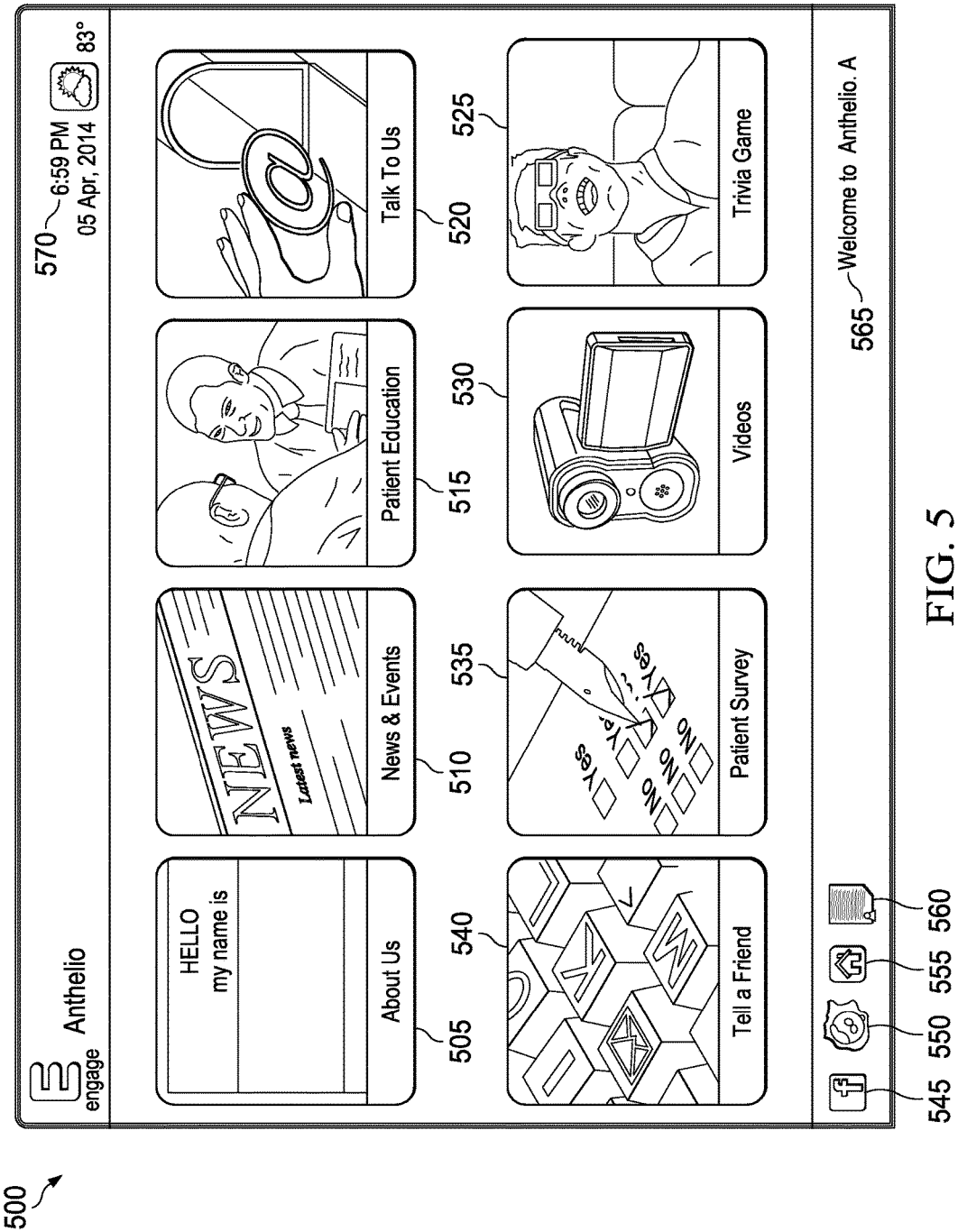
FIG. 5 is a diagram of an embodiment of a patient engagement point of service application user interface.

FIG. 5 is a diagram of an embodiment of the POS patient engagement application user interface 500. The POS patient engagement application user interface 500 may contain links to modules of the POS patient engagement application 300. While eight links are shown, any number of links may be displayed based upon configurations and capabilities of the device displaying POS patient engagement application user interface 500. About us link 505 may provide access to about us module 306; news and event link 510 may provide access to news and events module 315; patient education link 515 may provide access to patient education module 308; talk to us link 520 may provide access to talk to us module 322; trivia game link 525 may provide access to trivia module 330; videos link 530 may provide access to video module 328; patient survey link 535 may provide access to patient survey module 326; and tell a friend link 540 may provide access to tell a friend module 324. Other links not pictured may be present in some embodiment to allow access to the modules of POS patient engagement application 300.

At the footer of the POS patient engagement application user interface 500 several shortcuts may be displayed. The displayed shortcuts may be configured by the user, the customer, a developer of the POS patient engagement application, or any other interested party. While four shortcuts are shown, any number and type may be displayed based upon configurations and capabilities. Facebook shortcut 545 may allow a user to access the customer's Facebook page, or a user Facebook page. Twitter shortcut 550 may allow a user to view the customer's twitter feed or some other twitter feed. Home shortcut 555 may allow the user to return to the home page from whatever module they may currently be using. Code of conduct shortcut 560 may provide access to the POS patient engagement application code of conduct that governs conduct of users and customers in relation to the POS patient engagement application. Also at the footer, a ticker 565 may be displayed. Content of the ticker may be configured by the customer using the about us 205 module of the patient engagement hub 200.

In the header of the POS patient engagement application user interface 500 the current time and date may be displayed. Other useful information may be provided to the user, e.g. current weather conditions. In some embodiments, the POS patient engagement application user interface 500 may comprise different numbers and types of links, headers, footer, and/or layouts based upon preferences of users, customers, or application providers.

Figure 6:
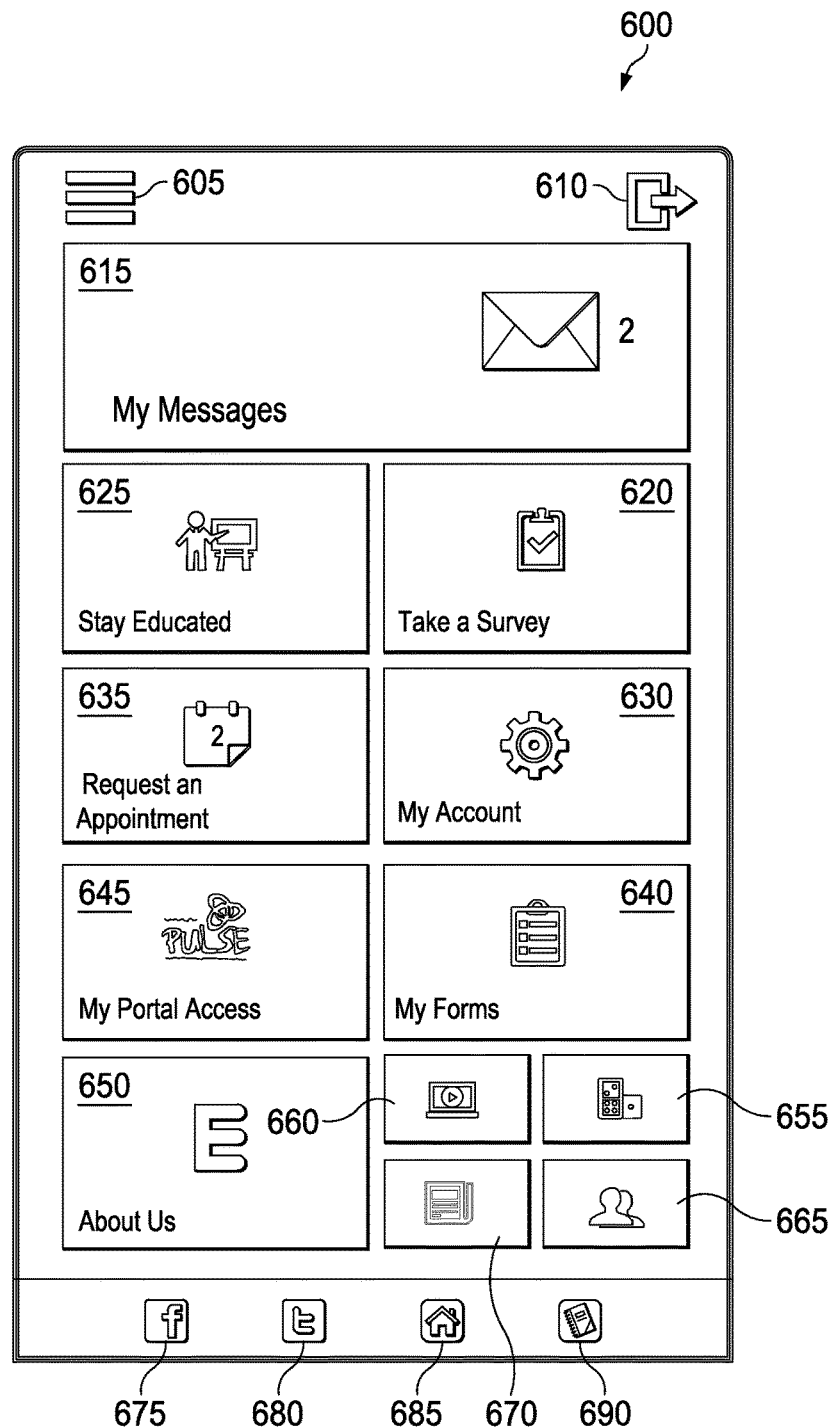
FIG. 6 is a diagram of an embodiment of a patient engagement mobile application user interface.

FIG. 6 is a diagram of a mobile patient engagement application user interface 600. Mobile patient engagement application user interface 600 may contain links to modules of the mobile patient engagement application 400. While twelve links are shown, any number of links may be displayed based upon configurations and capabilities of the device displaying mobile patient engagement application user interface 600. Menu link 605 may provide access to a menu of options and a complete menu of modules that may be accessed by mobile patient engagement application user interface 600. Logout link 610 may allow a user to logout of the mobile patient engagement application. My messages link 615 may allow a user to access the my messages module 408; take a survey link 620 may provide access to the patient survey module 418; stay educated link 625 may provide access to the patient education module 410; my account link 630 may provide access to the my account module 422; request an appointment link 635 may provide access to the appointment request module 420; my forms link 640 may provide access to the patient notification module 426; my portal access link 645 may provide access to a custom tile module 424; about us link 650 may provide access to about us module 436; trivia link 655 may provide access to the trivia module 440; videos link 660 may provide access to the video module 438; tell a friend link 665 may provide access to the tell a friend module 444; and news and events link 670 may provide access to the news and events module 442.

Facebook shortcut 675 may allow a user to access the customer's Facebook page, or a user Facebook page. Twitter shortcut 680 may allow a user to view the customer's twitter feed or some other twitter feed. Home shortcut 685 may allow the user to return to the home page from whatever module they may currently be using. Code of conduct shortcut 690 may provide access to the mobile patient engagement application code of conduct that governs conduct of users and customers in relation to the mobile patient engagement application.

Figure 7:
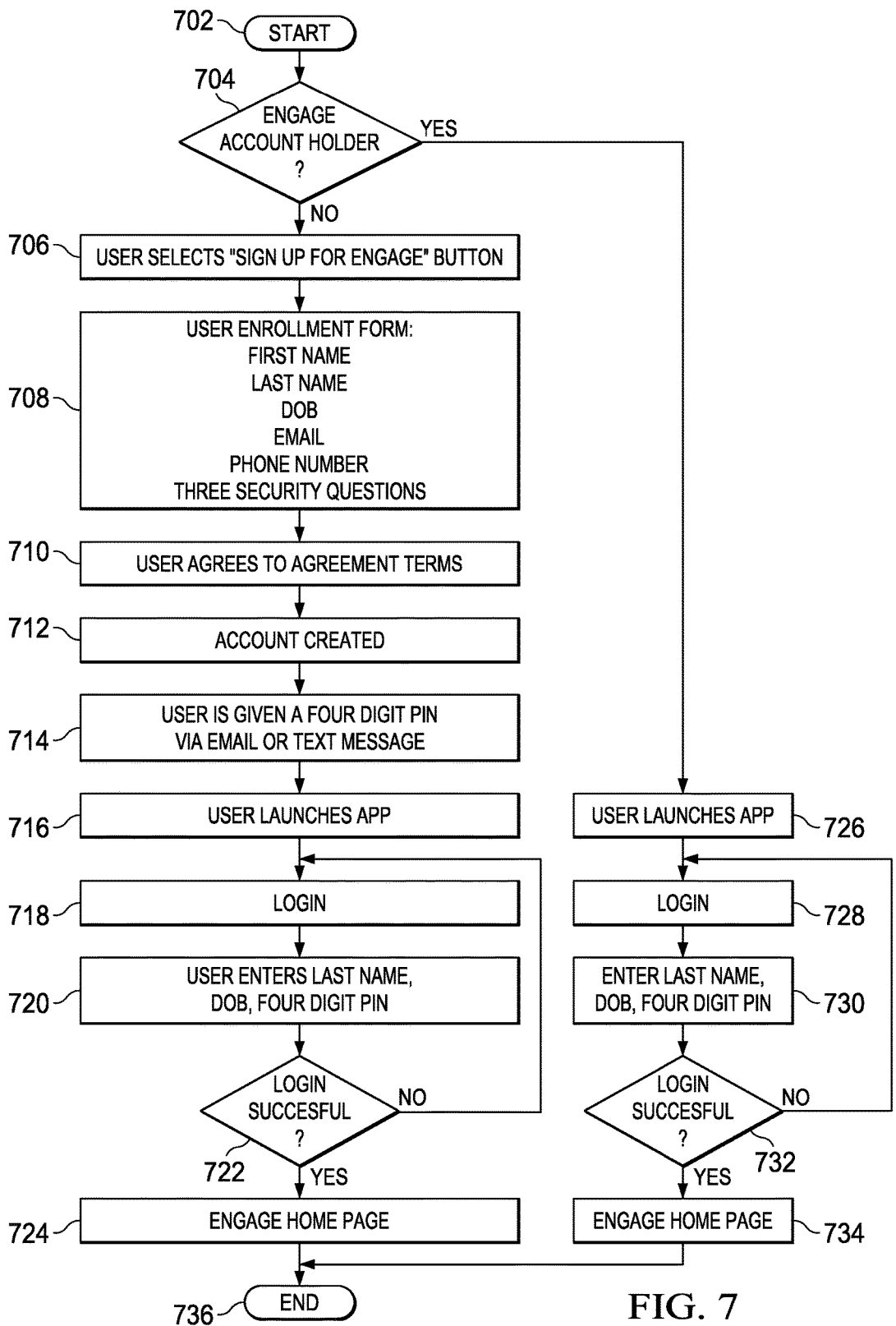
FIG. 7 is a flow diagram of an embodiment of a patient engagement enrollment process.

FIG. 7 is a flow diagram of a method for enrolling a user by the patient engagement system. The method begins at step 702. At step 704 a determination may be made whether the user is a current account holder. If the user is not an account holder, the user may select to sign up for an account at step 706. At step 708, the user may complete an enrollment form. At step 710, the user may agree to any agreement terms. At step 712, the user account may be created. At step 714, the user may be provided with a PIN number via text message, email, or some other communication medium. At step 716, the user may launch the mobile patient engagement applications. At step 718, the user may be prompted to log into the user account. At step 720, the user may enter user credentials for log in. At step 722, a determination may be made as to whether the supplied credential are correct; if no, the user may be returned to the login prompt at step 718. If the credentials are successful, the user may be presented with the patient engagement application user interface at step 724. If at step 704, the user indicates that they have an account, the patient engagement application may be launched at step 726. At step 728, the user may be prompted to log into the user account. At step 730, the user may enter user credentials for log in. At step 732, a determination may be made as to whether the supplied credential are correct; if no, the user may be returned to the login prompt at step 728. If the credentials are successful, the user may be presented with the patient engagement application user interface at step 734. The process may end at step 736.

Figure 8:
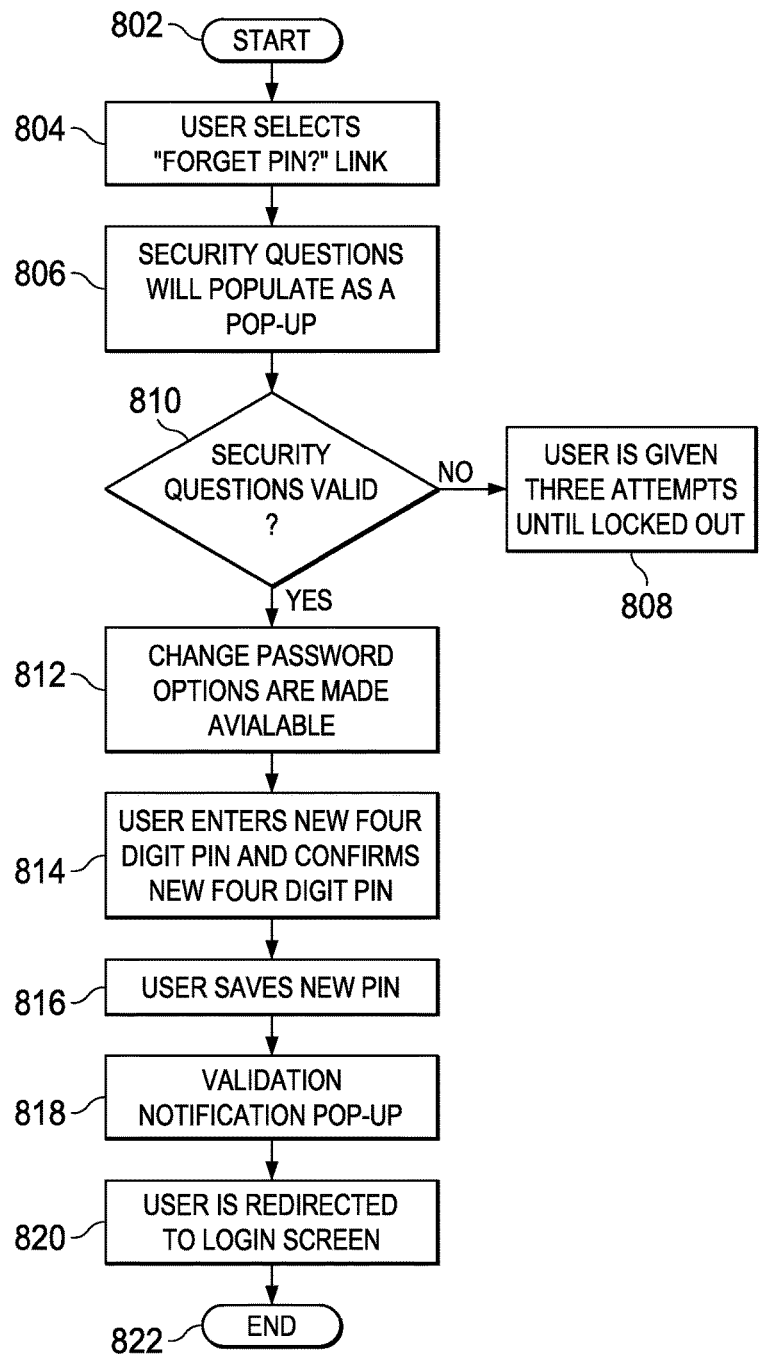
FIG. 8 is a flow diagram of an embodiment of a patient engagement PIN recovery process.

FIG. 8 is a flow diagram of an embodiment of a PIN recovery method for the patient engagement application. The method begins at step 802 when a user forgets their PIN. At step 804 the user may select a "forgot PIN" link. At step 806 one or more security questions may be presented to the user as a pop-up window. At step 810, the answers provided to the security questions may be evaluated. If the answers are not correct, the user is given up to three attempts to retry at step 808. If the answers are still incorrect after the third attempt, the user account associated with the PIN will be locked. If the answers provided are correct, the change password options are made available to the user at step 812. At step 814, the user may select and confirm a new PIN. At step 816, the new PIN may be saved. At step 818, a validation notification pop-up may be displayed. As step 820, the user may be redirected to the login screen. The method may end at step 822.

Figure 9:
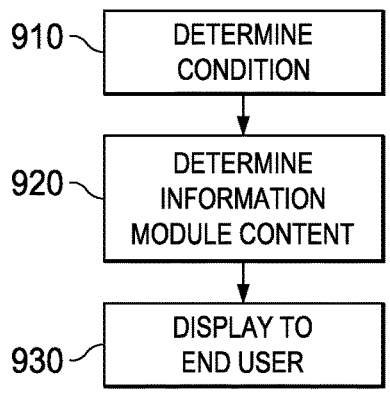
FIG. 9 is a flow diagram of an embodiment of a patient engagement media presentation process.

FIG. 9 is a flow diagram of a method of providing trivia and education to a user. At step 910, a condition associated with the user may be determined. The condition may be one that the user suffers from, or has suffered from in the past. The condition may also be one that the user is interested in but has not suffered from. The condition may also be one that is treated by a customer that the user may be visiting. The determination may be made by a customer or some other automated process. Once the condition is determined, information module content associated with the condition may be determined at step 920. The determination may be made by a customer or some other automated process. At step 930, the information module content may be displayed to the user. The display of the trivia and/or educational materials may be via related modules on either the POS patient engagement application and/or the mobile patient engagement application.

Figure 10:
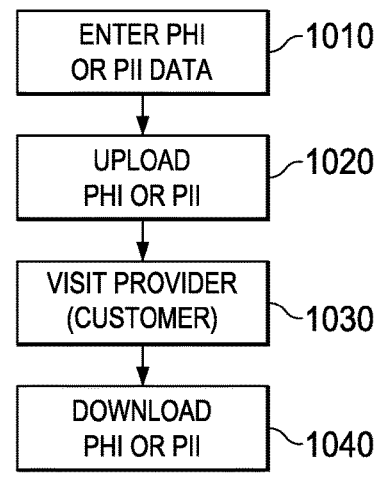
FIG. 10 is a flow diagram of an embodiment of a patient engagement form completion process.

FIG. 10 is a flow diagram of an embodiment of providing personally identifiable information and/or protected health information. At step 1010 protected health information and/or personally identifiable information may be entered into a HIPAA compliant device. At step 1020 the protected health information and/or personally identifiable information may be uploaded to a HIPAA compliant data storage, e.g. user data 155. At step 1030 the user may visit a customer, e.g. at customer site 105. The customer may require the user to complete various forms for treatment. In this case, rather than reenter all the personally identifiable information and/or protected health information into the forms, the user may download the previously stored protected health information and/or personally identifiable information into the form at step 1040. This may speed the wait times the user may face when visiting a new customer location.

Figure 11:
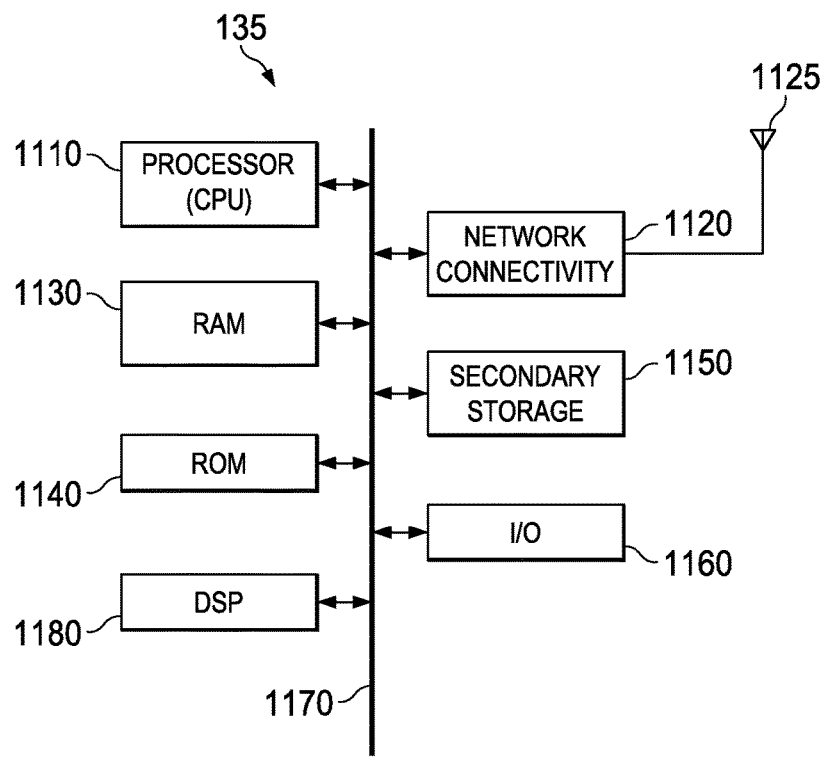
FIG. 11 is a block diagram of an embodiment of a patient engagement hub.

FIG. 11 is a block diagram of an embodiment of a patient engagement hub 135. Patient engagement hub 135 includes a processor 1110 suitable for implementing embodiments disclosed herein. The processor 1110 may control the overall operation of the patient engagement hub 135 through operating instructions stored in a computer readable medium in order to effect the methods described in this application. In addition to the processor 1110 (which may be referred to as a central processor unit or CPU), the patient engagement hub 135 might include network connectivity devices 1120, random access memory (RAM) 1130, read only memory (ROM) 1140, secondary storage 1150, and input/output (I/O) devices 1160. These components might communicate with one another via a bus 1170. In some cases, some of these components may not be present or may be combined in various combinations with one another or with other components not shown. These components might be located in a single physical entity or in more than one physical entity. Any actions described herein as being taken by the processor 1110 might be taken by the processor 1110 alone or by the processor 1110 in conjunction with one or more components shown or not shown in the drawing, such as a digital signal processor (DSP) 1180. Although the DSP 1180 is shown as a separate component, the DSP 1180 might be incorporated into the processor 1110. The processor 1110 executes instructions, codes, computer programs, or scripts that it might access from the network connectivity devices 1120, RAM 1130, ROM 1140, or secondary storage 1150 (which might include various disk-based systems such as hard disk, floppy disk, and/or optical disk). While only one CPU 1110 is shown, multiple processors may be present. Thus, while instructions may be discussed as being executed by a processor, the instructions may be executed simultaneously, serially, or otherwise by one or multiple processors. The processor 1110 may be implemented as one or more CPU chips and may be a hardware device capable of executing computer instructions.

The network connectivity devices 1120 may take the form of modems, modem banks, Ethernet devices, universal serial bus (USB) interface devices, serial interfaces, token ring devices, fiber distributed data interface (FDDI) devices, wireless local area network (WLAN) devices, radio transceiver devices such as code division multiple access (CDMA) devices, global system for mobile communications (GSM) radio transceiver devices, universal mobile telecommunications system (UMTS) radio transceiver devices, long term evolution (LTE) radio transceiver devices, worldwide interoperability for microwave access (WiMAX) devices, and/or other well-known devices for connecting to networks. These network connectivity devices 1120 may enable the processor 1110 to communicate with the Internet or one or more telecommunications networks or other networks from which the processor 1110 might receive information or to which the processor 1110 might output information. The network connectivity devices 1120 might also include one or more transceiver components 1125 capable of transmitting and/or receiving data wirelessly. The patient engagement hub 135 may communicate with user mobile device 125 and router 110 via network connectivity devices 1120 through internet 130.

The RAM 1130 might be used to store volatile data and perhaps to store instructions that are executed by the processor 1110, e.g. instructions required to execute the application front end 140, or user interface 202. The ROM 1140 is a non-volatile memory device that typically has a smaller memory capacity than the memory capacity of the secondary storage 1150. ROM 1140 might be used to store instructions and perhaps data that are read during execution of the instructions. Access to both RAM 1130 and ROM 1140 is typically faster than to secondary storage 1150. The secondary storage 1150 is typically comprised of one or more disk drives or tape drives and might be used for non-volatile storage of data or as an over-flow data storage device if RAM 1130 is not large enough to hold all working data. Secondary storage 1150 may be used to store programs that are loaded into RAM 1130 when such programs are selected for execution. Secondary storage 1150 may be used to store application data 145, customer data 150, and/or user data 155.

The I/O devices 1160 may include liquid crystal displays (LCDs), touch screen displays, keyboards, keypads, switches, dials, mice, track balls, voice recognizers, card readers, paper tape readers, printers, video monitors, or other well-known input/output devices. User interface 202 may be displayed to a customer via I/O devices 1160. Also, the transceiver 1125 might be considered to be a component of the I/O devices 1160 instead of or in addition to being a component of the network connectivity devices 1120.

As previously described, Messaging module 222 may interact with modules at the POS engagement application 300 via messages module 308, or the mobile patient engagement application 400 via messages module 408. These interactions may enable secure messaging between a user and customer and other third-parties approved by the user. The parties to the secure communication may include hospitals, front offices, physician offices, physicians, care teams, x-ray clinics, labs, diagnostic providers, pharmacies, home care providers, device vendors, insurance offices, social workers, or any other party that may have a need to know about a user's medical information. With consent of a user, secure messages may be shared with other healthcare professionals, or friends and family that may support the user. For example, a user may pose a question to a doctor. With the user's permission, the doctor may add a nurse practitioner to the messaging conversation to assist the user in answering the question. The user may give consent in real time as the conversation is occurring, or the user may preapprove certain individuals for inclusion on the secure messages. This example allows the question to be answered in a more efficient manner and frees up the doctor to handle other tasks.

In some embodiments, a customer may create messages and send them to groups of users based upon selectable characteristics of the users. The characteristics may be demographic, for example the customer may wish to send a message to all male users over fifty years of age. The characteristics may be related to medical conditions, for example, the customer may wish to send a message to all users with hypertension. Other possible characteristics may include: treating physician, discharge data, practice type visited, etc. Additional characteristics may be implemented as required by the customer.

Secure messaging may offer users, authorized third-parties, and customers the ability to communicate securely and electronically via the patient engagement hub 200. A bidirectional framework may be utilized such that correspondence may be initiated by either the user or the customer. Secure messages may be sent in real-time in a protected and structured format content, which standard email may not provide. The secure messaging function may comply with HIPAA requirements and may also satisfy Measure 17 of Meaningful Use Stage 2 requirements. Messages may be transmitted using symmetric encryption technology as well as SHA-1 hashing algorithms, or other encryption techniques as required.

Composing a secure message may indicate that the user is transmitting their personal health information to a third-party who has a Direct domain address outside of the portal system. Transmitting to a customer or contact outside of the patient portal via Direct secure messaging may contribute to the ability of the portal to perform and comply with the view, download, and transmit criteria for meaningful use stage 2 of the Direct protocol. When "Compose Encrypted Email" or some other similar message composition option is selected, the patient may be required to enter a Direct domain address which the system may validate is a valid Direct domain address. Direct messages may be based on an encryption standard used for exchanging health information via electronic communications. Direct messaging may use a Direct address similar to an email address recognizable and routable by a Health Information Service Provider (HISP). Within the secure message, users may attach their personal health profile in various formats including consolidated clinical document architecture (CCDA) format, lab results, care plans, inpatient referral summaries, and transition of care plans from within the patient engagement hub 200, or they may attach a file from within their own files. Upon submission of a secure message, the user may receive confirmation of the message being sent successfully.

Secure messaging may build a communication layer for all electronic communications between all the stake holders involved in patient care delivery. Secure messaging may play an important role in improving user access to customers. Secure messaging may also help users who want to be better informed and more active members of their care team. Secure messaging may be used to: promote care coordination between visits, handle routine health issues, address user questions and concerns, monitor user conditions, adjust the care plan in a timely manner, and help users better manage their condition.

Secure messaging system may also allow users to communicate with a customer in an unpressured setting that fits their schedule. Users may avoid the frustration of trying to reach a customer by phone. Instead, secure messaging may provide easier access to a customer. Users may feel more comfortable discussing sensitive health issues via secure messaging rather than in person. Users may follow up with questions they may have forgotten or didn't have time to ask during a clinic visit. Also, users may review the customer's response whenever it is convenient. Users may share important information for managing their health condition(s), such as blood pressure or blood glucose levels. Users may be able to use secure messaging to stay in touch with customers who are caring for family members, such as an older parent or relative. Secure messages may be configured such that only a user's health care team, such as health care providers and specific clinic staff, may read the user's messages Secure messaging may be a convenient cost-effective means for customers to communicate with users. Secure messaging may reduce "telephone tag" (leaving repeated messages) which may result in delays in communication and/or miscommunication of information. Customers may address a variety of routine health issues more efficiently, freeing up time for additional office visits and increasing access for users who need to be seen. In addition, customers may triage user messages, thus more pressing needs and questions may be addressed sooner. Customers may also batch answers by replying to a group of similar questions all at once, which may improve efficiency and save additional time if auto-replies are used for routine issues.

Figure 12:
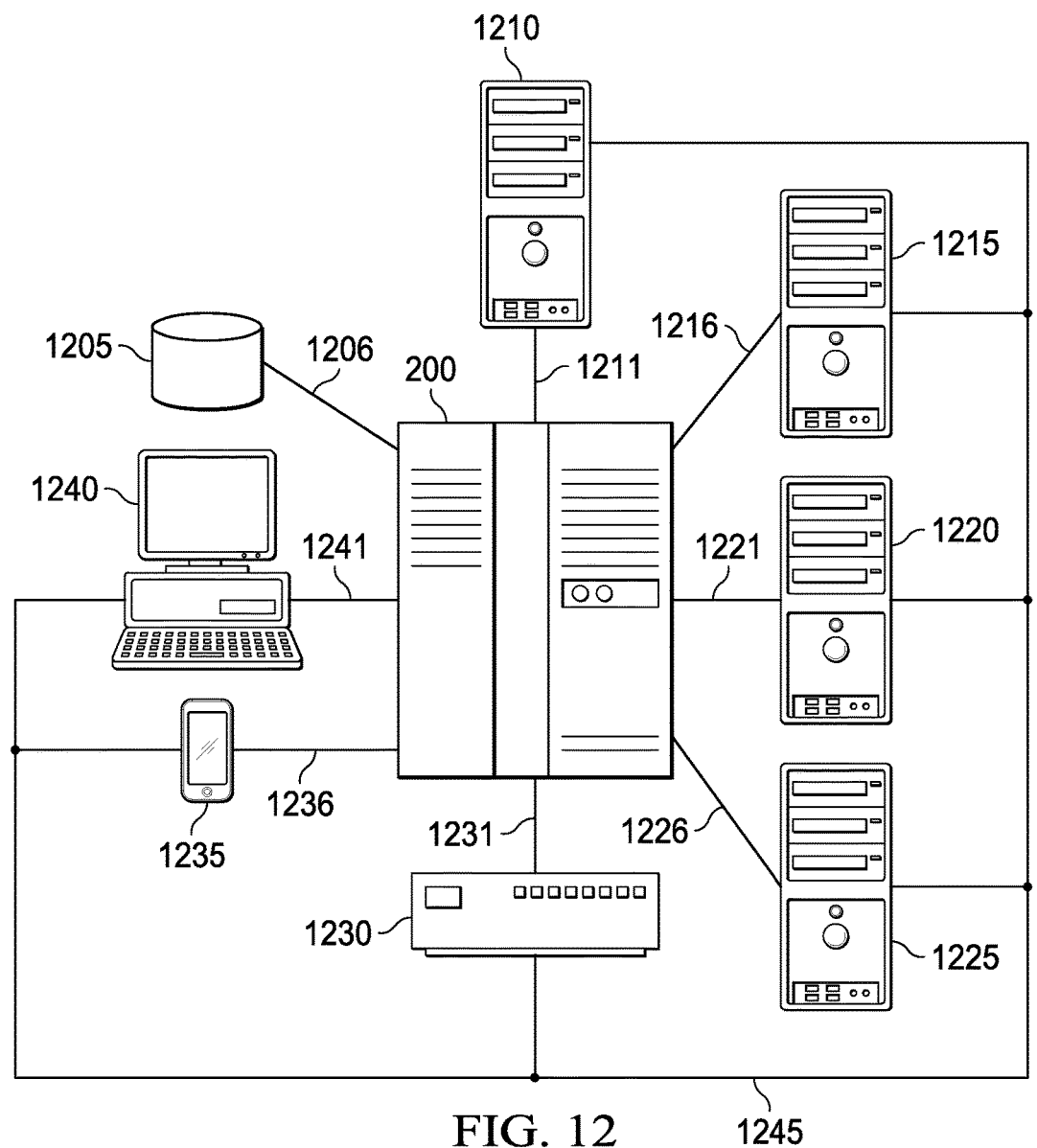
FIG. 12 is a diagram of an embodiment of a system for secure messaging.

Turning now to FIG. 12, an embodiment of a system for secure messaging is shown. The system may comprise a patient engagement hub 200. Patient engagement hub 200 may be configured for both Direct communications and secure in-network encrypted messages. Direct communications messages may be based on an encryption standard used for exchanging health information via electronic communications. Direct messaging may use a Direct address similar to an email address recognizable and routable by a Health Information Service Provider (HISP) 1230. In-network secure messages may be transmitted to devices residing within the same network as patient engagement hub 200. Thus, patient engagement hub 200 may seamlessly communicate with both in-network devices via secure messaging and out of network devices using Direct messaging. Patient engagement hub 200 may be configured to facilitate direct secure Messaging using HISP through Direct messaging as well as in-network secure messaging. A message may be determined as an in-network secure message or Direct through HISP by the patient engagement hub 200 based on configuration settings requested by users during the implementation of the patient engagement hub 200.

The patient engagement hub 200 may interact with a data store 1205 via secure connection 1206. Secure connection 1206 may be an encrypted transmission line in-network with the patient engagement hub 200. In some embodiments, data store 1205 may reside on the patient engagement hub 200. Data store 1205 may be used to store free text versions of messages transmitted through patient engagement hub 200. Data store 1205 may also be used to store structured versions of the free text messages. The structured versions may include metadata for searching and classifying messages. The data store 1205 may contain other electronic medical records and data according to requirements set by users of the system.

A patient device 1240 may communicate with the patient engagement hub 200 via a secure encrypted connection 1241 when patient device 1240 is in-network with the patient engagement hub 200. If the patient device 1240 is out of network with the patient engagement hub 200, the patient device 1240 may communicate with the patient engagement hub 200 via a message exchange capability, for example, HISP 1230 using Direct messages along communication line 1245. While only one patient device 1240 is pictured, any number of patient devices may communicate with the patient engagement hub 200 as described.

A family member device 1235 may communicate with the patient engagement hub 200 via a secure encrypted connection 1236 when family member device 1235 is in-network with the patient engagement hub 200. If the family member device 1235 is out of network with the patient engagement hub 200, the family member device 1235 may communicate with the patient engagement hub 200 via a message exchange capability, for example, HISP 1230 using Direct messages along communication line 1245. While only one family member device 1235 is pictured, any number of family member devices may communicate with the patient engagement hub 200 as described.

A pharmacy server 1210 may communicate with the patient engagement hub 200 via a secure encrypted connection 1211 when pharmacy server 1210 is in-network with the patient engagement hub 200. If the pharmacy server 1210 is out of network with the patient engagement hub 200, the pharmacy server 1210 may communicate with the patient engagement hub 200 via a message exchange capability, for example, HISP 1230 using Direct messages along communication line 1245. While only one pharmacy server 1210 is pictured, any number of pharmacy servers may communicate with the patient engagement hub 200 as described.

A provider server 1215 may communicate with the patient engagement hub 200 via a secure encrypted connection 1216 when provider server 1215 is in-network with the patient engagement hub 200. If the provider server 1215 is out of network with the patient engagement hub 200, the provider server 1215 may communicate with the patient engagement hub 200 via a message exchange capability, for example, HISP 1230 using Direct messages along communication line 1245. While only one provider server 1215 is pictured, any number of provider servers may communicate with the patient engagement hub 200 as described. Providers may include hospitals, physicians, clinics, labs, care teams or other medical service providers.

A payer server 1220 may communicate with the patient engagement hub 200 via a secure encrypted connection 1221 when payer server 1220 is in-network with the patient engagement hub 200. If the payer server 1220 is out of network with the patient engagement hub 200, the payer server 1220 may communicate with the patient engagement hub 200 via a message exchange capability, for example, HISP 1230 using Direct messages along communication line 1245. While only one payer server 1220 is pictured, any number of payer servers may communicate with the patient engagement hub 200 as described. Payers may include clearance houses, insurance companies, or any other entity that makes payments for medical services.

An ancillary server 1225 may communicate with the patient engagement hub 200 via a secure encrypted connection 1226 when ancillary server 1225 is in-network with the patient engagement hub 200. If the ancillary server 1225 is out of network with the patient engagement hub 200, the ancillary server 1225 may communicate with the patient engagement hub 200 via a message exchange capability, for example, HISP 1230 using Direct messages along communication line 1245. While only one ancillary server 1225 is pictured, any number of ancillary servers may communicate with the patient engagement hub 200 as described. Ancillary entities may include medical supply vendors or other entities ancillary to medical treatment processes.

Figure 13:
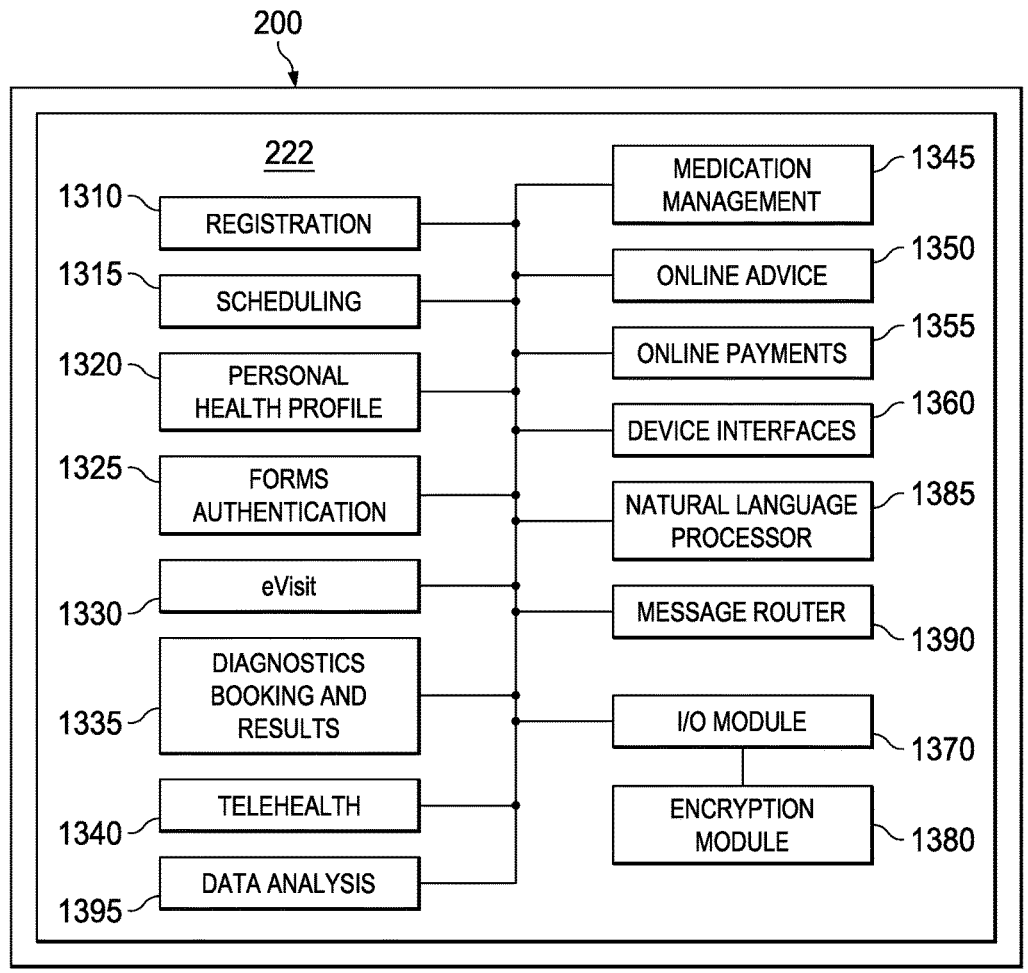
FIG. 13 is a functional block diagram of an embodiment of a secure messaging module.

FIG. 13 is a functional block diagram of an embodiment of messaging module 222. Messaging module 222 may be a component of patient engagement hub 200. While certain modules are depicted within messaging module 222 in this embodiment, other embodiments may comprise a subset of these modules or additional modules as required by users of the system. Registration module 1310 may be configured to receive registration information from users of the secure messaging system. Users may agree to use the secure messaging system by acknowledging an agreement as part of the registration module 1310. Third-parties customers may also register with the system using registration module 1310. Users may use registration module 1310 to authorize customers and third-parties to communicate with them using the secure messaging system. To ensure secure messaging, the messaging module 222 may prevent messaging between users and others until they have registered with registration module 1310. When a third party registers, they may be prevented from communicating until the user approves communication with them. Thus, the secure message capability may be accessed in several ways including but not limited to: a user may add others to an existing conversation, a user may preapprove others to initiate conversations, a customer or third-party may request user approval to join or add others to a conversation. In each case, the user may be required to approve anyone prior to them being added to a conversation.

Scheduling module 1315 may provide a secure means for a user to schedule medical appointments. Using secured messaging for scheduling may enable the user to provide additional information in the appointment request, e.g. information usually prevented from transmission due to HIPAA requirements. For example, a user may request an appointment and include details about symptoms they are experiencing and/or other personal health information.

Personal health profile module 1320 may securely communicate with a user to view and modify their electronic health profile. The electronic health profile may contain personal health information of a user, e.g., allergies, medications, vital statistics. The user may authorize customers or other third parties to view the electronic health profile to aid in treatment and/or diagnosis or for other reasons as necessary.

Forms authentication module 1325 may securely communicate with a user to view and/or edit various medical forms. The forms may contain protected health information. The forms authentication module 1325 may also securely communicate with a user to electronically sign their forms using an e-signature that is secure and traceable to the user. The forms authentication module may comply with various e-signature regulations to ensure the validity and legal effect of any forms signed electronically.

eVisit module 1330 may enable a user to have a virtual visit with a customer. The eVisit module 1330 may use audio, video, text, or any other form of messaging to enable a user and customer to have a real time conversation in a secure environment. The eVisit module 1330 may be configured to allow third parties to join the conversion between the customer and the user, for example an in-home caregiver or consultant may join in the conversation to receive information related to care of the user. eVisit module 1330 may also be used to provide prescriptions, collect payments, or other interactions between the user and/or the customer and/or others.

Diagnostics booking and results module 1335 may communicate with a user to facilitate scheduling of various diagnostic appointments for the user. For example a user may schedule labs or x-rays via diagnostics booking and results module 1335. The scheduling may be accomplished without the need to call a primary care provider and therefore free up time for the primary care provider, while concurrently allowing a user to schedule the diagnostics at a time convenient to them. After the diagnostic appointment is completed, the results may be provided to the user via the diagnostics booking and results module 1335. The user may also choose to share the results with others via the diagnostics booking and results module 1335, e.g., a customer or other third party.

Telehealth module 1340 may enable various telehealth features to be utilized by the user. Telehealth module 1340 may include the use of electronic communication to support long-distance clinical health care, health-related education, and various health care administration functions. Telehealth module 1340 may be configured to conform to various government regulatory telehealth guidelines.

Medication management module 1345 may include features to allow a user to manage various medications they are using. Medication management module 1345 may enable a customer to send prescriptions to a user. Medication management module 1345 may also allow a customer to view current medications of a user to ensure that no harmful interactions occur form the use of various drugs. Medication management module 1345 may alert a user to possible side effects of various drugs. Medication management module 1345 may also be configured to remind a user to take certain drugs according to a prescribed schedule. Medication management module 1345 may also be used by the user to request refills of prescriptions as required.

Online advice module 1350 may provide the user access to various online advice sources. The online advice may include health tips that are automatically tailored specifically to the user based upon information gathered from other modules of the messaging module 222 or patient engagement hub 200. The user may also perform keyword searches or pose specific inquiries to find advice related to topics of their choosing. The user may choose to share the advice they receive with others via secure messaging.

Online payments module 1355 may send invoices to a user. Online payments module 1355 may also receive payments from a user. Online payments module 1355 may also send bills to other parties that may be responsible for payment. Online payments module 1355 may receive payment from other sources upon approval of the other sources by the user.

Device interfaces module 1360 may enable messaging module 222 to communicate with various devices. The various devices may include medical treatment and/or health monitoring devices running a variety of operating systems. Device interfaces module 1360 may gather relevant data from the medical treatment and/or health monitoring devices and add the gathered data to the patient's electronic health record. In some cases, this gathered data may be provided directly to a healthcare provider monitoring treatment.

Natural language processor 1385 may receive free text unstructured messages received by the patient engagement hub 200. Natural language processor 1385 may convert the free text unstructured messages to structured data with metadata tags. The metadata tags may be used for searching archived messages. The metadata tags may also be used in analysis of archived messages. Natural language processor 1385 is described in greater detail below.

Message router 1390 may receive messages from patients and route them to the appropriate recipients based upon the contents of the message or certain attributes selected by the sender during message creation. Message router 1390 may determine whether to use secure encrypted messaging within the patient engagement hub 200 network, or a Direct message for users outside of the patient engagement hub 200 network. Message router 1390 may consult a directory or other listing of addresses in order to determine whether a message should be transmitted as a Direct message or an in-network secure message. In some embodiments, other modules may consult a directory or comprise logic for determining whether the message should be transmitted as a Direct message or an in-network secure message. Message router 1390 functionality is described in greater detail below.

Data analysis module 1395 may analyze messages for use in gathering statistics on a group of patients, specific patients, types of illnesses, or any other metric desired to be analyzed by a user of the messaging system. Data analysis module 1395 is described in greater detail below.

I/O module 1370 may interact with the other modules of the messaging module 222 to facilitate communication external to the messaging module 222. I/O module may receive data for transmission from the various modules and proceed to transmit the outbound information to the encryption module 1380. Encryption module 1380 may encrypt transmissions leaving the messaging module 222. Likewise, secure communications may be received from a user's mobile device or computer. The encryption module 1380 may receive the secure communication and decrypt as necessary. The decrypted message may then be transmitted to the I/O module 1370 which may then transmit the message to the appropriate module of messaging module 222. Encryption module 1380 may communicate outside of the patient engagement hub 200 via I/O devices 1160.

The messaging module 222 may automatically capture and document communications between users and customers in the user's electronic health records (EHR), thereby improving record accuracy. By automatically updating the electronic heath record, human error may be removed from the process significantly improving the treatment received by a user.

Figure 14:
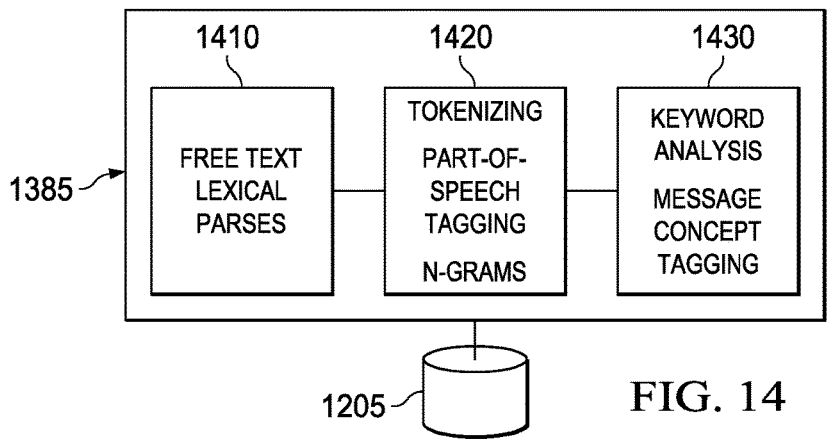
FIG. 14 is a block diagram of an embodiment of a natural language processor.

Turning now to FIG. 14, a block diagram of an embodiment of natural language processor 1385 is shown. Natural language processor 1385 may comprise a free text lexical parser 1410. Parser 1410 may receive an unstructured free text message sent by a user of the messaging module 222. Parser 1410 may input the unstructured free text as a string of characters and output a structure of words or phrases that are then fed into tokenizer 1420. Tokenizer 1420 receives the partially structured output of parser 1410 and tokenizes the data. The tokens may be part-of speech, n-grams, or any other token that may be used to facilitate analysis of the information contained in the unstructured free text message. Once the tokens have been identified, keyword analyzer 1430 may perform analysis on the now structured message. The keyword analysis may be used to tag the concept of the message. For example, the analysis may determine that the concept of the message is an appointment request, a description of symptoms, or some other type of message that may be received by messaging module 222. In some embodiments, unstructured messages and structured messages may be stored in data store 1205 for future analysis and/or archival purposes. In some embodiments, structured or unstructured messages may be appended to a patient's electronic medical record.

Figure 15:
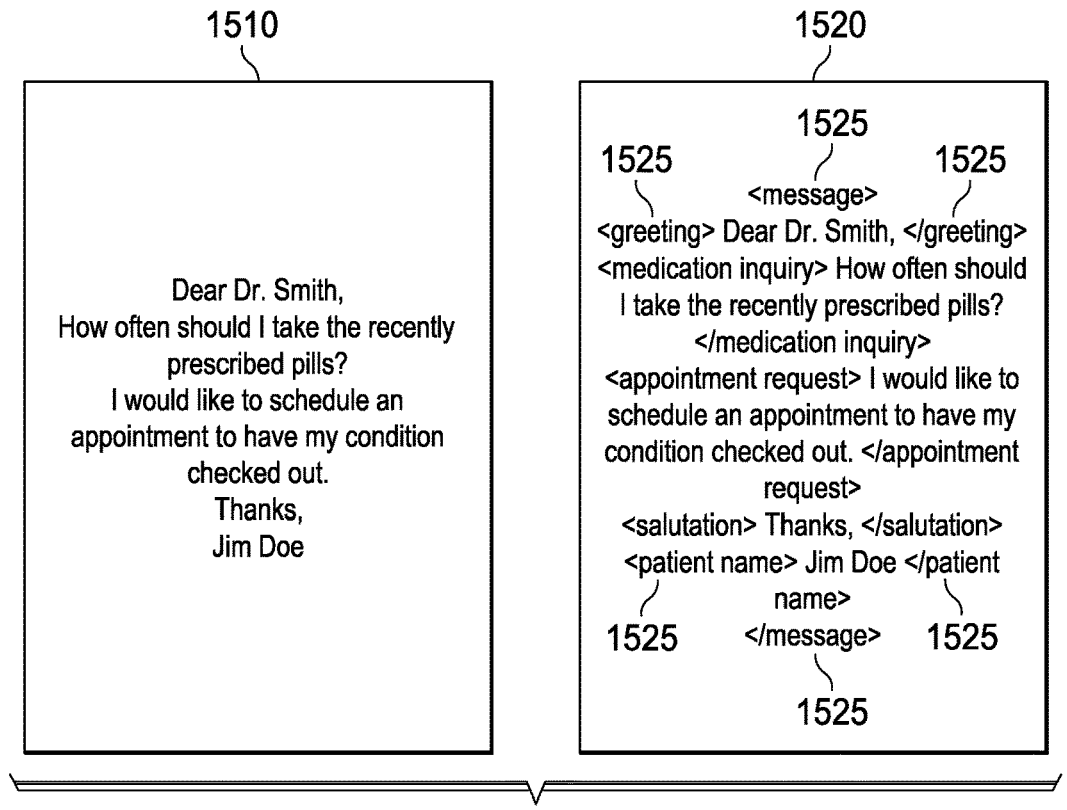
FIG. 15 is a diagram of an unstructured message and a corresponding structured message.

FIG. 15 is a diagram of an unstructured message 1510 and a corresponding structured message 1520. Unstructured message 1510 may be received by natural language processor 1385 and structured message 1520 may be output by natural language processor 1385. Unstructured message 1510 may be any unstructured free text message, for example an email or text message. Unstructured message 1510 may also be a transcript of a real-time electronic messaging session. Structured message 1520 may contain a number of metadata tags 1525. Metadata tags 1525 may be inserted into the structured message 1520 by tokenizer 1420 or keyword analyzer 1430. Metadata tags 1525 may be used to identify specific concepts within the message. For example, a "greeting" tag may indicate a greeting within the message. Greetings may be searched or parsed for identifiers of the sender of a message. A "medication inquiry" tag may be used to indicate that a question has been asked about a medication. These fields may be further searched for a type of medication or other medication related information. An "appointment request" tag may be used to indicate that the sender has requested an appointment. In some embodiments, the presence of certain tags may automatically trigger an action by the patient engagement hub 200. For example, the presence of an appointment request tag may trigger the creation of an appointment reservation or automatically notify an appointment scheduler. While several tags are depicted in FIG. 1520, any number of tags may be used and defined according to the needs of users of the secure messaging system.

Figure 16:
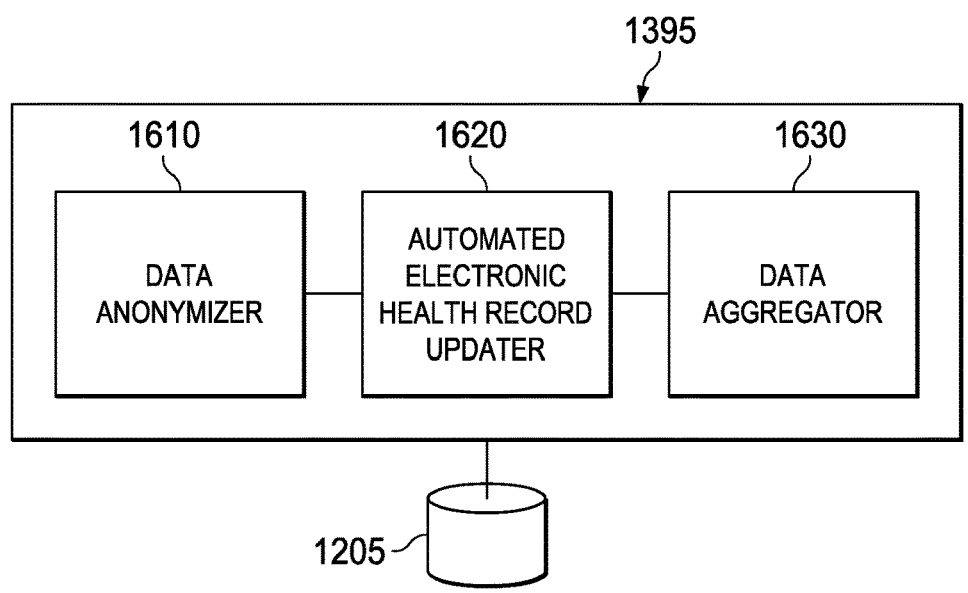
FIG. 16 is a block diagram of an embodiment of a data analysis module.

FIG. 16 is a block diagram of an embodiment of a data analysis module 1395. Data analysis module 1395 may comprise a data anonymizer 1610, an automated electronic health record (EHR) updater 1620, and a data aggregator 1630. In some embodiments, the secure messages may anonymized by data anonymizer 1610. For example, identifying information of a user may be removed from the structured secure message. The identifying information may be located within the structured message using the metadata tags 1525. In this case, the data remaining after the message has been anonymized may be harvested and stored in data store 1205 or some other storage medium. The gathered data may aggregated by data aggregator 1630 and may be used to identify trends in treatment or conditions experienced by users. The gathered data may also be used by providers to aid in preparing responses to common inquiries of users. For example, a doctor may be able to see all messages that have been transmitted that include the word diabetes using the metadata tags 1525. In this case, the messages may be anonymized by removing any user identifiers and only the information related to diabetes would be available, the messages (or portions of the messages) that mention diabetes may then be aggregated by data aggregator 1630. The doctor may then use this information to prepare common answers that may be provided to other users when they ask a frequently asked question.

Figure 17:
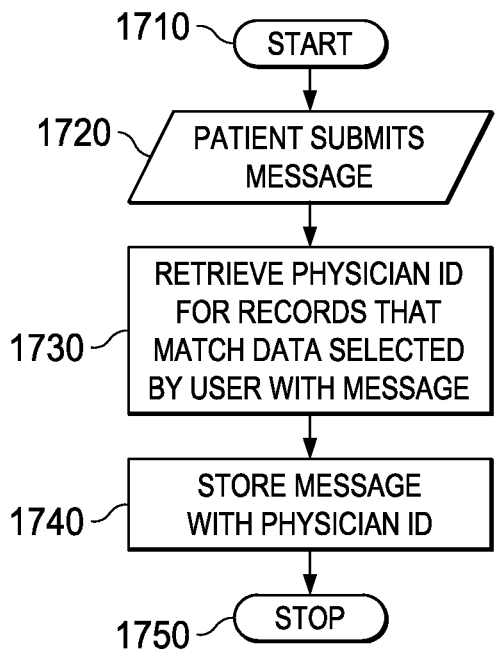
FIG. 17 is a flow diagram of an embodiment of a process for routing messages at the messaging module.

FIG. 17 is a flow diagram of an embodiment of a process for routing messages at the messaging module 222. At step 1720, a patient may submit a message to the messaging module 222. The message may be received by the message router 1390. Message router 1390 may analyze attributes of the message. These attributes may be based on metadata tags 1525 or selections made by the sender of the message while composing the message. The attributes may include facility, practice, department, or other attributes of the message. Message router 1390 may retrieve a physician identification from data store 1205 or some other data storage device based upon the attributes selected by the sender of the message at step 1730. At step 1740, the message router 1390 may store the message in data store 1205 or some other data storage device associated with the physician identification. The process ends at step 1750.

Figure 18:
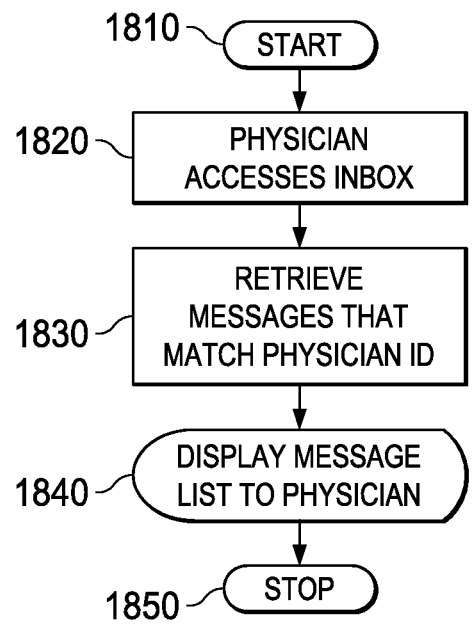
FIG. 18 is a flow diagram of an embodiment of a process for retrieving messages at the messaging module.

FIG. 18 is a flow diagram of an embodiment of a process for retrieving messages at the messaging module 222. At step 1820, a physician or other user of the messaging module 222 may login to patient engagement hub 220 and access their inbox. At step 1830, message router 1390 may retrieve messages that have been tagged with the physician identification of the physician. The retrieved messages may be displayed to the physician at step 1840. The process ends at step 1850.

While various embodiments in accordance with the disclosed principles have been described above, it should be understood that they have been presented by way of example only, and are not limiting. Thus, the breadth and scope of the invention(s) should not be limited by any of the above-described exemplary embodiments, but should be defined only in accordance with the claims and their equivalents issuing from this disclosure. Furthermore, the above advantages and features are provided in described embodiments, but shall not limit the application of such issued claims to processes and structures accomplishing any or all of the above advantages.

Various terms used herein have special meanings within the present technical field. Whether a particular term should be construed as such a "term of art," depends on the context in which that term is used. "Connected to," "in communication with," or other similar terms should generally be construed broadly to include situations both where communications and connections are direct between referenced elements or through one or more intermediaries between the referenced elements, including through the Internet or some other communicating network. "Network," "system," "environment," and other similar terms generally refer to networked computing systems that embody one or more aspects of the present disclosure. These and other terms are to be construed in light of the context in which they are used in the present disclosure and as those terms would be understood by one of ordinary skill in the art would understand those terms in the disclosed context. The above definitions are not exclusive of other meanings that might be imparted to those terms based on the disclosed context.

Words of comparison, measurement, and timing such as "at the time," "equivalent," "during," "complete," and the like should be understood to mean "substantially at the time," "substantially equivalent," "substantially during," "substantially complete," etc., where "substantially" means that such comparisons, measurements, and timings are practicable to accomplish the implicitly or expressly stated desired result.

Additionally, the section headings herein are provided for consistency with the suggestions under 37 C.F.R. 1.77 or otherwise to provide organizational cues. These headings shall not limit or characterize the invention(s) set out in any claims that may issue from this disclosure. Specifically and by way of example, although the headings refer to a "Technical Field," such claims should not be limited by the language chosen under this heading to describe the so-called technical field. Further, a description of a technology in the "Background" is not to be construed as an admission that technology is prior art to any invention(s) in this disclosure. Neither is the "Summary" to be considered as a characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of such claims shall be considered on their own merits in light of this disclosure, but should not be constrained by the headings herein.

What is claimed is:

1. An engagement hub for secure messaging and structuring of unstructured electronic messages, the engagement hub comprising:
  a natural language processor in communication with a hub data repository; and
  an engagement hub processor comprising a patient education module and a data analyzer,
  wherein the natural language processor is configured to structure an unstructured electronic message received at the engagement hub via network connectivity devices, the unstructured electronic message comprising routing characteristics,
  wherein the data analyzer of the engagement hub processor is configured to analyze the stored structured message;
    determine the presence of a payer claim metadata tag;

receive approval of a claim; and
transmit the approval to a payer,
wherein the patient education module of the engagement hub processor is configured to access health videos and user defined customizable educational information from the hub data repository and to execute instructions which cause said health videos and user defined customizable health information to be output to a display for engaging patients to improve health education, and
wherein structuring the unstructured electronic message comprises
using a lexical parser to parse free text within the unstructured electronic message;
tokenizing the parsed free text into a plurality of tokens representing components of the parsed free text;
performing a keyword analysis of the tokenized parsed free text and generating a tag identifying a message concept based on the keyword analysis;
generating message component n-grams based on the plurality of tokens representing the components of the parsed free text;
coding each of the plurality of tokens with one of a plurality of metadata tags based on an analysis of the plurality of tokens, said ones of the metadata tags indicating message components of the plurality of tokens;
generating a structured electronic message corresponding to the unstructured electronic message, the structured electronic message comprising the plurality of tokens, the message concept tag, and the plurality of metadata tags; and
storing the structured electronic message in the hub data repository,
wherein said plurality of metadata tags is associated with patient medical information.

2. The engagement hub of claim 1, further comprising:
a message router in communication with the network connectivity devices and the hub data repository, the message router being configured to
receive a second unstructured electronic message comprising one or more routing characteristics, the routing characteristics selected by a sender of the second unstructured electronic message during creation of the second unstructured electronic message;
determine one or more recipients of the second unstructured electronic message based upon the routing characteristics;
associate the second unstructured electronic message with user identifiers of the one or more recipients; and
store the second unstructured electronic message in the hub data repository with the user identifiers.

3. The engagement hub of claim 2, wherein the message router is further configured to:
receive a user identifier;
retrieve stored unstructured electronic messages associated with the user identifier; and
display the retrieved unstructured electronic messages.

4. The engagement hub of claim 1,
wherein the engagement hub processor is further configured to:
receive an outbound electronic message for transmission to one or more recipients;
determine for each of the one or more recipients whether they are in a network of the engagement hub;
if the recipient is in the network, encrypt the outbound electronic message and transmit the outbound electronic message to an in-network recipient via an encrypted connection; and
if the recipient is not in the network, transmit the outbound electronic message using a secure protocol to an out of network recipient.

5. The engagement hub of claim 4, wherein the secure protocol is Direct messaging protocol, and the outbound electronic message is transmitted to a Health Information Service Provider (H ISP) prior to transmission to the out of network recipient.

6. The engagement hub of claim 1, wherein the data analyzer is further configured to:
remove, by a data anonymizer, personally identifiable information and protected health information from the structured electronic message; and
aggregate, using a data aggregator, a plurality of anonymized structured electronic messages, the plurality of structured electronic messages comprising a common token.

7. The engagement hub of claim 1, wherein the data analyzer is further configured to:
aggregate, using a data aggregator, a plurality of structured electronic messages, the plurality of structured electronic messages comprising a common token; and
transmit an outbound electronic message to senders of each of the plurality of structured electronic message.

8. The engagement hub of claim 1, wherein the data analyzer is further configured to:
analyze the stored structured message;
determine the presence of an appointment request metadata tag;
automatically generate an appointment request; and
transmit the appointment request to a scheduler.

9. The engagement hub of claim 1, wherein the data analyzer is further configured to:
analyze the stored structured message;
determine the presence of a refill request metadata tag;
receive approval of a refill request; and
automatically transmit the refill request to a pharmacy.

10. A method in an engagement hub for secure messaging and structuring of unstructured electronic messages using a natural language processor, the method comprising:
receiving at the engagement hub via network connectivity devices, an unstructured electronic message comprising routing characteristics;
using a lexical parser of the natural language processor to parse free text within the unstructured electronic message;
tokenizing the parsed free text into a plurality of tokens representing components of the parsed free text;
performing a keyword analysis of the tokenized parsed free text and generating a tag identifying a message concept based on the keyword analysis;
generating message component n-grams based on the plurality of tokens representing the components of the parsed free text;
coding each of the plurality of tokens with one of a plurality of metadata tags based on an analysis of the plurality of tokens, the ones of the metadata tags indicating message components of the plurality of tokens;
generating a structured electronic message corresponding to the unstructured electronic message, the structured electronic message comprising the plurality of tokens, the message concept tag, and the plurality of metadata tags;

storing the structured electronic message in a hub data repository;

analyzing, using a data analyzer of the engagement hub, the stored structured message;

determining the presence of a payer claim metadata tag;

receiving approval of a claim; and transmitting the approval to a payer, wherein the engagement hub further comprises a patient education module comprising health videos and user defined customizable educational information for engaging patients to improve health education, and wherein said plurality of metadata tags is associated with patient medical information.

11. The method of claim 10 further comprising:

receiving, at a message router, a second unstructured electronic message comprising one or more routing characteristics, the routing characteristics selected by a sender of the second unstructured electronic message during creation of the second unstructured electronic message;

determining one or more recipients of the second unstructured electronic message based upon the routing characteristics;

associating the second unstructured electronic message with user identifiers of the one or more recipients; and storing the second unstructured electronic message in the hub data repository with the user identifiers.

12. The method of claim 11 further comprising:

receiving, at the message router, a user identifier;

retrieving stored unstructured electronic messages associated with the user identifier; and displaying the retrieved unstructured electronic messages.

13. The method of claim 10, further comprising:

receiving, at said engagement hub, an outbound electronic message for transmission to one or more recipients;

determining for each of the one or more recipients whether they are in a network of the engagement hub;

if the recipient is in the network, encrypting the outbound electronic message and transmitting the outbound electronic message to an in-network recipient via an encrypted connection; and if the recipient is not in the network, transmitting the outbound electronic message using a secure protocol to an out of network recipient.

14. The method of claim 13, wherein the secure protocol is Direct messaging protocol, and the outbound electronic message is transmitted to a Health Information Service Provider (HISP) prior to transmission to the out of network recipient.

15. The method of claim 10 further comprising:

removing, by a data anonymizer, personally identifiable information and protected health information from the structured electronic message; and aggregating, using a data aggregator, a plurality of anonymized structured electronic messages, the plurality of structured electronic messages comprising a common token.

16. The method of claim 10 further comprising:

aggregating, using a data aggregator, a plurality of structured electronic messages, the plurality of structured electronic messages comprising a common token; and transmitting an outbound electronic message to senders of each of the plurality of structured electronic message.

17. The method of claim 10, further comprising:

analyzing, by the data analyzer, the stored structured message;

determining the presence of an appointment request metadata tag;

automatically generating an appointment request; and transmitting the appointment request to a scheduler.

18. The method of claim 10, further comprising:

analyzing, by the data analyzer, the stored structured message;

determining the presence of a refill request metadata tag;

receiving approval of a refill request; and automatically transmitting the refill request to a pharmacy.

* * * * *